US005709861A

United States Patent [19]
Santiago et al.

[11] Patent Number: 5,709,861
[45] Date of Patent: *Jan. 20, 1998

[54] COMPOSITIONS FOR THE DELIVERY OF ANTIGENS

[75] Inventors: Noemi B. Santiago, Hawthorne; Susan Haas, Monsey, both of N.Y.; Andrea Leone-Bay, Ridgefield, Conn.; Sam J. Milstein, Larchmont; Evgueni Barantsevitch, New Rochelle, both of N.Y.

[73] Assignee: Emisphere Technologies, Inc., Hawthorne, N.Y.

[*] Notice: The term of this patent shall not extend beyond the expiration date of Pat. No. 5,451,410 and 5,629,020.

[21] Appl. No.: 372,208

[22] Filed: Jan. 13, 1995

Related U.S. Application Data

[63] Continuation-in-part of Ser. No. 51,019, Apr. 22, 1993, Pat. No. 5,451,410, and a continuation-in-part of Ser. No. 231,622, Apr. 22, 1994, Pat. No. 5,629,020.

[51] Int. Cl.$^6$ .................................................. A61K 39/00
[52] U.S. Cl. ..................... 424/184.1; 424/451; 424/489; 514/553; 514/561
[58] Field of Search ........................ 424/184.1, 489, 424/451; 514/553, 561

[56] References Cited

U.S. PATENT DOCUMENTS

| Re. 24,899 | 11/1960 | Green . | |
| 2,671,451 | 3/1954 | Bolger | 128/260 |
| 2,862,918 | 12/1958 | Meyer et al. | 260/123.5 |
| 2,868,740 | 1/1959 | Luce | 260/8 |
| 2,971,916 | 2/1961 | Schleicher et al. | 252/62.5 |
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |

(List continued on next page.)

FOREIGN PATENT DOCUMENTS

| 1077842 | 8/1976 | Canada | A61K 9/50 |
| 0 000 667 A1 | 2/1979 | European Pat. Off. | A61K 9/50 |
| 0 036 145 A1 | 9/1981 | European Pat. Off. | A61K 31/62 |
| 0 068 314 | 1/1983 | European Pat. Off. | . |
| 0 105 804 | 4/1984 | European Pat. Off. | C12N 15/00 |
| 0 130 162 A2 | 1/1985 | European Pat. Off. | B01J 13/02 |
| 0 170 540 A1 | 2/1986 | European Pat. Off. | A61K 9/52 |
| 0 342 054 A2 | 11/1989 | European Pat. Off. | A61K 7/06 |
| 0 342 056 A2 | 11/1989 | European Pat. Off. | A61K 7/06 |
| 0 616 799 A1 | 9/1994 | European Pat. Off. | A61K 7/00 |
| 1 351 358 | 3/1964 | France . | |
| 1 468 601 | 2/1967 | France . | |

(List continued on next page.)

OTHER PUBLICATIONS

Airaudo, C.B. et al. (1987) *Journal of Food Science*, vol. 52(6), pp. 1750–1752.
Andini, S. et al. (1975) *Origins of Life*, vol. 6, pp. 147–153.
Brooke, S. 1 et al. (1977) *BioSystems*, vol. 9, pp. 1–22.
Chen et al. (1975) "Evidence for Hemiacetal Formation", *Biochemistry*, vol. 18, No. 5, pp. 921–925.
Davis et al. (1983) "Leucinal Inhibits . . . ", *Pharmacology Biochemistry Behavior*, vol. 19, pp. 791–794.
Dose, K. (1974) *Origins of Life*, vol. 5, pp. 239–252.
Fasman et al. (1964) *Biochemistry*, vol. 3, No. 11, pp. 1665–1674.
Fox, S.W. et al. (1976) *BioSystems*, vol. 8, pp. 40–44.
Fox, S.W. et al, *Molecular Evolution and the Origin of Life*, Maxel Decker, New York (1977).

(List continued on next page.)

*Primary Examiner*—Ponnathapura Achutamurthy
*Attorney, Agent, or Firm*—Darby & Darby

[57] ABSTRACT

The present invention relates to the delivery of antigens. Delivery systems are provided that include the antigen and acylated or sulfonated amino acids or poly amino acids. Methods of preparation and administration of these compositions are also provided.

13 Claims, 8 Drawing Sheets

U.S. PATENT DOCUMENTS

| | | | |
|---|---|---|---|
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/231.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,961 | 12/1993 | Mathiowitz et al. | 427/213.31 |
| 5,278,148 | 1/1994 | Branca et al. | 514/19 |
| 5,310,535 | 5/1994 | Kruper et al. | 424/1.1 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,379 | 2/1995 | Dirix et al. | 424/451 |
| 5,418,010 | 5/1995 | Janda et al. | 427/213.31 |
| 5,451,410 | 9/1995 | Milstein et al. | 424/490 |
| 0 365 183 | 4/1990 | European Pat. Off. | A61K 31/18 |
| 0 366 277 | 5/1990 | European Pat. Off. | A61K 9/107 |
| 0 418 642 | 3/1991 | European Pat. Off. | |
| 0 448 057 | 9/1991 | European Pat. Off. | C12P 21/08 |
| 0 452 161 | 10/1991 | European Pat. Off. | A61K 7/48 |
| 0 459 795 | 12/1991 | European Pat. Off. | A61K 37/02 |
| 0 467 389 | 1/1992 | European Pat. Off. | A61K 9/52 |
| 0 490 549 A1 | 6/1992 | European Pat. Off. | A61K 47/12 |
| 0 517 211 A1 | 9/1992 | European Pat. Off. | A61K 47/12 |

FOREIGN PATENT DOCUMENTS

| | | | |
|---|---|---|---|
| 2 133 926 | 12/1972 | France | A61K 27/00 |
| 2 326 934 | 5/1977 | France | A61K 47/00 |
| 2 565 102 | 12/1985 | France | A61K 9/52 |
| 2 424 169 | 12/1974 | Germany | A61K 9/00 |
| 3 202 255 | 10/1982 | Germany | C08L 89/00 |
| 3 612 102.9 | 10/1986 | Germany | C07K 15/00 |
| 71258/2 | 12/1987 | Israel | |
| 48-24246 | of 1973 | Japan | |
| 56-68612 | 6/1981 | Japan | A61K 31/19 |
| 58-35111 | of 1983 | Japan | A61K 9/66 |
| 280825 | 12/1964 | Netherlands | |
| 280826 | 12/1964 | Netherlands | |
| B-146698 | 11/1982 | Norway | A61K 37/26 |
| 1236885 | of 0000 | United Kingdom | |
| 929401 | 6/1963 | United Kingdom | |
| 1075952 | 8/1967 | United Kingdom | |
| 1 567 763 | 5/1980 | United Kingdom | A61K 9/22 |
| 2 095 994 | 10/1982 | United Kingdom | |
| WO 85/02772 | of 0000 | WIPO | A61K 49/00 |
| WO 85/00105 | 1/1985 | WIPO | A61K 9/52 |
| WO85/00110 | 1/1985 | WIPO | A61K 47/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/14420 | 7/1994 | WIPO | A61K 9/16 |

| | | | |
|---|---|---|---|
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |

OTHER PUBLICATIONS

Fox, S.W. et al. (1968) *Biochim. Biophys. Acta*, vol. 160, pp. 246–249.

Fox, S.W. (1976) *Origins of Life*, vol. 7, pp. 49–68.

Fox, S.W. (1980) *Naturwissenschaften*, vol. 67, pp. 378–383.

Fox, S.W. et al, (1960) *Archives of Biochemistry and Biophysics*, vol. 86, pp. 281–285.

Fox, S.W. et al. (1974) *Origins of Life*, vol. 5, pp. 227–237.

Fox, S.W. (1984) *Origins of Life*, vol. 14, pp. 485–488.

Gol'dovskii A.M. (1978) *Zhurnal Evolyutsionnoi Biokhimii i Fiziologii*, vol. 14(6), pp. 517–519.

Gurrieri, S. et al. (1973) *Thermochimica Acta*, vol. 7, pp. 231–239.

Harada, K. et al. (1979) *BioSystems*, vol. 11, pp. 47–53.

Harada et al., (1960) *Archives of Biochemistry and Biophysics*, vol. 86, pp. 274–280.

Hare (1970) *Etude Cenetique De La Polycondensation Thermique D'$_X$-Amino Acides*, vol. 45, pp. 330–339.

Heinrich, M.R. et al. (1969) *Archives of Biochemistry and Biophysics*, vol. 130, pp. 441–448.

Heinz, B. et al. (1981) *BioSystems*, vol. 14, pp. 33–40.

Hennon, G. et al. (1975) *Biochimie*, vol. 57, pp. 1395–1396.

Hsu, L.L. et al. (1976) *BioSystems*, vol. 8, pp. 89–101.

Hsu, L.L. et al. (1971) *Currents in Modern Biology*, vol. 4, pp. 12–25.

Ishima, Y. et al. (1981), *BioSystems*, vol. 14, pp. 243–251.

Jackson et al. (1991) "Pharmacological . . . ", *J. Pharm. & Exp. Thera.*, vol. 261, No. 1, pp. 546–552.

Jungck, J.R. et al. (1973) *Naturwissenschaften*, vol. 60, pp. 425–427.

Kokufuta, E. et al. (1984) *BioSystems*, vol. 16, pp. 175–181.

Krampitz, G. et al. (1967) *Naturwissenschaften*, pp. 516–517.

Krampitz, G. et al. (1968) *Naturwissenschaften*, pp. 345 and 346.

Krampitz, G. et al. (1966) *Naturwissenschaften*, pp. 7 and 8.

Lacey, Jr., J.C. et al. (1979) *BioSystems*, vol. 11, pp. 9–17.

Lacey, Jr., J.C. et al. (1979) *BioSystems*, vol. 11, pp. 1–7.

Martinez Luque–Romero, M. et al. (1986) *BioSystems*, vol. 19, pp. 267–272.

Masinovsky, Z. et al. (1989) *BioSystems*, vol. 22, pp. 305–310.

Matsuno, K. (1982) *BioSystems*, vol. 15, pp. 1–11.

Matsuno, K. (1984) *BioSystems*, vol. 17, pp. 11–14.

Matsuno, K. (1981) *BioSystems*, vol. 14, pp. 163–170.

McAlhaney, W.W. et al. (1976) *BioSystems*, vol. 8, pp. 45–50.

Melius, P. et al. (1987) *BioSystems*, vol. 20, pp. 213–217.

Melius, P. et al. (1975) *Bioorganic Chemistry*, vol. 4, pp. 385–391.

Melius, P. (1979) *BioSystems*, vol. 11, pp. 125–132.

Miquel, J. et al. (1971) *Currents in Modern Biology*, vol. 3, pp. 299–306.

Nakashima, T. et al. (1980) *J. Mol. Evol.*, vol. 15, pp. 161–168.

Nakashima, T. et al. (1981) *BioSystems*, vol. 14, pp. 151–161.

Novak, V.J.A. (1984) *Origins of Life*, vol. 14, pp. 513–522.

Olafsson, P.G. et al. (1971) *Polymer Letters*, vol. 9, pp. 521–528.

Phillips, R.D. et al. (1974) *Int. J. Peptide Protein Res.*, vol. 6, pp. 309–319.

Przybylski, A.T. et al. (1982) *Die Naturwissenschaften*, vol. 69, pp. 561–563.

Przybylski, A.T. et al. (1984) *Applied Biochemistry and Biotechnology*, vol. 10, pp. 301–307.

Przybylski, A.T. (1985) *BioSystems*, vol. 17, pp. 281–288.

Rohlfing, D.L. (1975) *Origins of Life*, vol. 6, pp. 203–209.

Rohlfing D.L. (1970) *Science*, vol. 169, pp. 998–1000.

Rohlfing, D.L. (1967) *Archives of Biochemistry and Biophysics*, vol. 118, pp. 468–474.

Rohlfing, D.L. et al. *Catalytic Activities of Thermal Polyanhydro–α–Amino Acids*, pp. 373–418.

Rohlfing, D.L. et al. (1976) *BioSystems*, vol. 8, pp. 139–145.

Ryan, J.W. et al. (1973) *BioSystems*, vol. 5, pp. 115–118.

Saunders, M.A. et al. (1974) *BioSystems*, vol. 6, pp. 81–92.

Snyder, W.D. et al. (1975) *BioSystems*, vol. 7, pp. 222–229.

Sokol, P.E. (1974) *Journal of the American Oil Chemists'Society*, vol. 52, pp. 101–102.

Tschager et al. (1988) *Milchwirtschaftliche Berichte*, vol. 95, pp. 79–83.

Vaughan, G. et al. (1987) *BioSystems*, vol. 20, pp. 219–223.

Vol'kenshtein, M.V. (1989) *Molekulyarnaya Biologiya*, vol. 23(1), pp. 23–37.

Waehneldt, T.V. et al. (1968) *Biochim. Biophys. Acta*, vol. 160, pp. 239–245.

Williams et al. (1991) *J. Biol. Chem.*, vol. 266, No. 8, pp. 5182–5190.

Yuki, A. et al. (1969) *Biochemical and Biophysical Research Communications*, vol. 36(4), pp. 657–663.

Zulaski et al. (1983) "New Carboxyalkyl Inhibitors of Brain Enkenphalinase", *J. Med. Chem.*, 26, pp. 60–65.

(1985) *Chemical Abstracts*, vol. No. 105(1), Abstract No. 12027p.

(1985) *Chemical Abstracts*, vol. No. 102(6), Abstract No. 50870d.

Chemical Abstract, vol. 80(9) Abst. No. 52392a.

Bergeron, Raymond J., et al. (1994) "Macromolecular Self–Assembly of Diketopiperazine Tetrapeptides", *Journal of the American Chemical Society*, vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood*, vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood*, vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry*, vol. 34, No. 7, pp. 2072–2078.

Bergeron, Raymond et al., "A Comparative Evaluation of Iron Clearance Models", *Annals New York Academy of Sciences*, pp. 378–393.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Airaudo, C.B., et al. (1987), *Journal of Food Science* 52(6):1750–1752.

Gelb, R., et al (1983), *Lite Sciences* 33(1):83–85.

Watterberg et al. (1988), *Pediatric Research*, vol. 23, No. 4, part 2, p. 570A, col. 1, abstract No. 2209.

Bernstein (1985), *Chest* 87(1):68S–73S.

Damage et al. (1988), *Diabetes* 37:246–251.

184360k, *Chemical Abstracts*:83 (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater.*, 20 (1993), Controlled Release Society, Inc.

X. Ma, et al., *Proceed. Intern. Symp. Control. Rel. Bioact. Mater.*, 20 (1993), Controlled Release Society, Inc. "IN VITRO Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.*, 20 (1993), Controlled Release Society, Inc.

Presented at *"IBC Rational Drug Design Conference"*, San Diego, Calif. –Dec. 1994.

Bergeron, Raymond J. et al., *J. Am. Chem. Soc.* 1994, 116,8479–8484 "Macromolecular Self–Assembly of Diketopiperazine Tetrapeptides".

Leone–Bay et al., Presented at *"Winter Conference on Medicinal and Bioorganic Chemistry"* Steamboat Springs, Colorado –Feb. 1995 Microsphere Formation and Drug Delivery in a Series of Derivatized Amino Acids.

Santiago et al. *Pharm. Res.* 11: 1994, p.S–298 "Oral Delivery of Heparin Microspheres made with Modified Amino Acids".

Leone–Bay et al., *Pharm. Res.* 11: 1994, p.S–121 "Oral Delivery of Heparin using Acylated Amino Acids".

Sarubbi et al., *Pharm. Res.* 11: 1994, p.S–299 "Oral Calcitonin Delivery using the PODDS Technology".

Leipold et al., *Pharm. Res.* 11: 1994, p.S–298 "Oral Delivery of Interferon in Rats and Primates".

Santiago et al., *Pharm. Res.* 11: 1994, p.S298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.*, 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.*, 19 (1992), Controlled Release Society, Inc., pp. 116–117.

Santiago et al. "Proteinoid Microspheres For The Oral Delivery of Heparin" *Proceed. Intern. Symp. Control. Rel. Bioact. Mater.*, 19 (1992), Controlled Release Society, Inc. pp. 514–515.

Santiago et al. *American Society for Microbiology* 92nd General Meeting, Abstract of the General Meeting, p. 159, May 26–30, 1992.

Milestein et al. "Preparation And In Vitro Characterization Of Proteinoid Microspheres" *Proceed Intern. Symp. Control. Rel. Bioact. Mater.*, 19 (1992), COntrolled Release Society, Inc. pp. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6TH Ann. Meeting and Expo.*, "Proteinoids –A Novel Drug Delivery System" Nov. 19, 1992, p.33.

Milstein et al., "Efficient Oral Delivery Of Monoclonal Antibodies By Proteinoid Encapsulation" *the 1993 Miami Bio/Technology Winter Symposium –Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting*, 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp.183–189, "Immunotherapy with Monoclonal Antibodies".

Michael E. Osband et al., Immunology Today, vol. 11, No.6 1990, pp. 93–95, "Problems in the investigational study and clinical use of cancer immunotherapy".

Tibtech Feb. 1993 vol.11, pp. 42–44 "Therapeutic antibodies –the coming of age".

Thoams A. Waldmann, Articles Jun. 21, 1991, pp. 1657–1662, "Monoclonal Antibodies in Diagnosis and Therapy".

Douglas et al., *Chemistry and Industry*, 22:748–751, 1985.

Finch, *Chemistry and Industry*, 22:752–756, 1985.

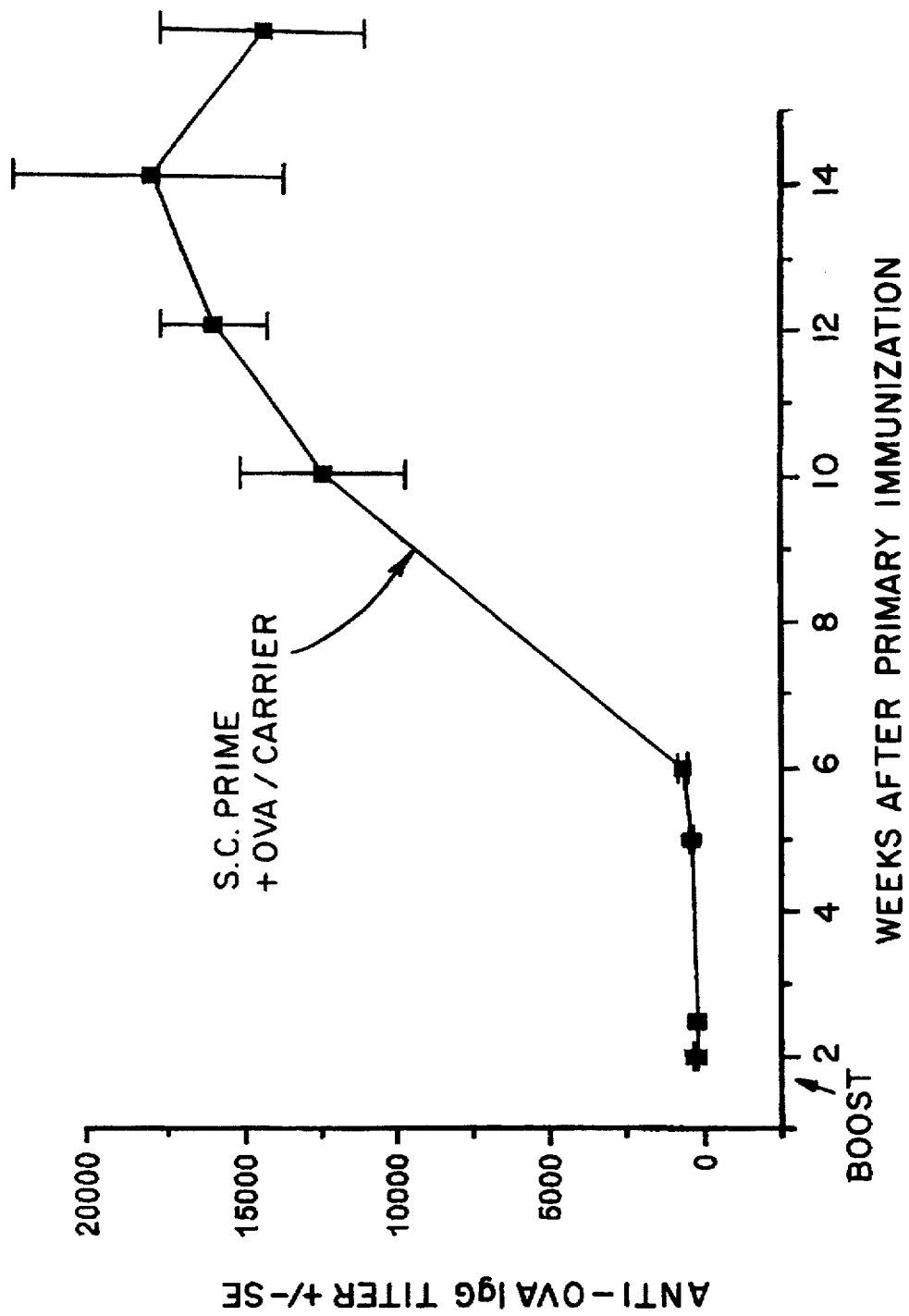

COMPOSITIONS FOR THE DELIVERY OF ANTIGENS

This is a continuation-in-part of application Ser. No. 08/051,019, filed Apr. 22, 1993, now U.S. Pat. No. 5,451,410, issued Sep. 19, 1995; and application Ser. No. 08/231,622, filed Apr. 22, 1994, now U.S. Pat. No. 5,629,020.

FIELD OF THE INVENTION

The present invention relates to compositions useful for the delivery, and preferably the oral delivery, of antigens. Methods for the preparation and for the administration of these compositions are also disclosed.

BACKGROUND OF THE INVENTION

Conventional means for delivering antigens to their intended targets are often severely limited by the presence of biological, chemical, and physical barriers. Typically, these barriers are imposed by the environment through which delivery must take place, the environment of the target for delivery, or the target itself.

Oral delivery to the circulatory system for many antigens would be the route of choice for administration to animals if not for physical barriers such as the mucus layer and the epithelial cells of the gastrointestinal (GI) tract. These barriers are relatively impermeable to certain antigens, but must be traversed before an antigen delivered via the oral route can reach the circulatory system.

Oral delivery is also impeded by chemical barriers such as the varying pH in the GI tract and the presence in the oral cavity and the GI tract of powerful digestive enzymes. Furthermore, orally administered soluble antigens can induce a non-responsive state or tolerance.

Methods for orally administering antigens have been previously developed which rely on the use of either attenuated microorganisms or polylactide/polyglycolide (PLA/PGA) microspheres to increase antigen presentation to and uptake by the appropriate antigen presenting cells. Attenuated organisms, unless properly delivered, can regain virulence, however. Additionally, broad spectrum use of PLA/PGA microspheres is not possible because these carriers require organic solvents that may alter or denature antigens. Furthermore, PLA/PGA systems are difficult to manufacture.

Recently, microspheres comprising artificial polymers of mixed amino acids (proteinoids) have been described for delivering biologically active agents including antigens. Santiago, et al. *Pharmaceutical Res.* Vol. 10, No. 8, (1993).

However, there is still a need in the art for simple, inexpensive, and easily prepared systems which can effectively deliver a broad range of antigens, particularly via the oral route.

SUMMARY OF THE INVENTION

Compositions useful in the delivery of antigens are provided. These delivery compositions comprise (a) an antigen; and (b) a carrier comprising a member selected from the group consisting of (i) an acylated amino acid; (ii) a poly amino acid comprising at least one acylated amino acid; (iii) a sulfonated amino acid; (iv) a poly amino acid comprising at least one sulfonated amino acid; or (v) a combination thereof.

BRIEF DESCRIPTION OF THE DRAWINGS

FIG. 8 is a graphic illustration of anti-OVA IgG titers induced in mice dosed with a subcutaneous prime of OVA antigen followed by an oral booster dose of OVA antigen and mixed sulfonated amino acids.

DETAILED DESCRIPTION OF THE INVENTION

Figure 1:
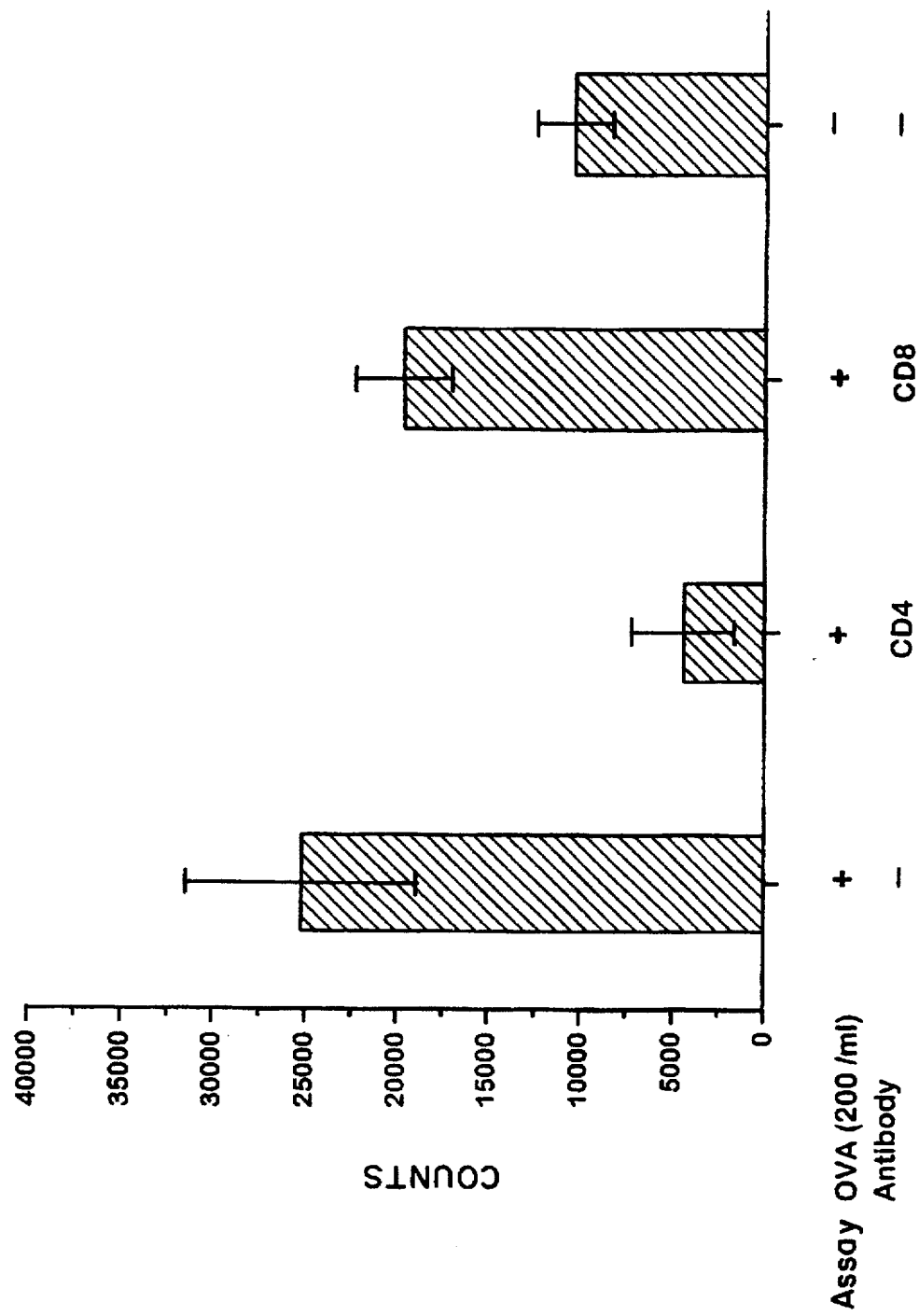
FIG. 1 is a graphic illustration of ovalbumin OVA antigen specific T cell proliferation after exposure to OVA antigen, of mouse spleen cells from mice dosed by oral gavage with OVA antigen and modified amino acid carrier. (Group 1 (6 priming doses)).

The present invention concerns the delivery of antigens through various biological, chemical, and physical barriers. The compositions of the present invention are particularly suited to the delivery of antigens which are subject to environmental or physiological degradation.

Other advantages provided by the present invention include the use of readily available or easy to prepare, inexpensive starting materials. The formulation methods of the present invention are cost-effective for preparing and isolating these compositions, are simple to perform, and are amenable to industrial scale up for commercial production.

The compositions of the invention are useful for administering antigens to animals including, but not limited to, birds and mammals such as, for example, primates and humans. The delivery compositions of the present invention elicit an immune response.

Antigens

Antigens suitable for use in the present invention include, but are not limited to, synthetic or naturally derived proteins and peptides; carbohydrates including, but not limited to, polysaccharides; lipids; and antigens isolated from biological sources such as, for example microbes, viruses, or parasites, and subunits or extracts therefrom; or any combination thereof. Special mention is made of the antigens *Streptococcus pneumoniae*, *S. typhi* VI carbohydrate, *Hemophilus influenzae* (type B), Acellular *B. pertussis*, *Neisseria meningiditis* (A,C), *H. influenzae* (type B, Hib), *Clostridium tetani* (tetanus), and *Corynebacterium diphtheriae* (diphtheria).

Carriers

Amino acids are the basic materials used to prepare the carriers useful in the present invention. An amino acid is any carboxylic acid having at least one free amine group and includes naturally occurring and synthetic amino acids. The preferred amino acids for use in the present invention are α-amino acids, and most preferably are naturally occurring α-amino acids. Many amino acids and amino acid esters are readily available from a number of commercial sources such as Aldrich Chemical Co. (Milwaukee, Wis, USA); Sigma Chemical Co. (St. Louis, Mo., USA); and Fluka Chemical Corp. (Ronkonkoma, N.Y., USA).

Representative, but not limiting, amino acids suitable for use in the present invention are generally of the formula

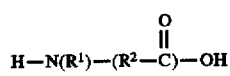     I wherein: $R^1$ is hydrogen, $C_1$–$C_4$ alkyl, or $C_2$–$C_4$ alkenyl;

$R^2$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl), or naphthyl ($C_2$–$C_{10}$ alkenyl);

$R^2$ being optionally substituted with $C_1$–$C_4$ alkyl, $C_2$–$C_4$ alkenyl, $C_1$–$C_4$ alkoxy, —OH, —SH, —$CO_2R^3$, $C_3$–$C_{10}$ cycloalkyl, $C_3$–$C_{10}$ cycloalkenyl, heterocyclic having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^2$ being optionally interrupted by oxygen, nitrogen, sulfur, or any combination thereof; and $R^3$ is hydrogen, $C_1$–$C_4$ alkyl, or $C_2$–$C_4$ alkenyl.

The preferred naturally occurring amino acids for use in the present invention as amino acids or components of a peptide are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, ε-carboxyglutamate, phenylglycine, or O-phosphoserine. The most preferred naturally occurring amino acids are arginine, leucine, lysine, phenylalanine, tyrosine, tryptophan, valine, and phenylglycine.

The preferred non-naturally occurring amino acids for use in the present invention are β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminophenyl acetic acid, aminophenyl butyric acid, γ-glutamic acid, cysteine, ε-lysine, ε-lysine, methionine sulfone, norleucine, norvaline, ornithine, d-ornithine, p-nitro-phenylalanine, hydroxy proline, 1,2,3,4,-tetrahydroisoquinoline-3-carboxylic acid, and thioproline.

Poly amino acids are either peptides or two or more amino acids linked by a bond formed by other groups which can be linked, e.g., an ester, anhydride or an anhydride linkage.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215. Special mention is made of di-peptide, tri-peptides, tetra-peptides, and penta-peptides, and particularly, the preferred peptides are di-peptides and tri-peptides. Peptides can be homo- or hetero- peptides and can include natural amino acids, synthetic amino acids, or any combination thereof.

Modified amino acids, poly amino acids, or peptides are either acylated or sulfonated and include amino acid amides and sulfonamides.

Acylated Amino Acids

Special mention is made of acylated amino acids having the formula

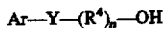     II wherein Ar is a substituted or unsubstituted phenyl or naphthyl;

Y is

$R^4$ has the formula

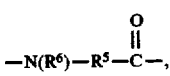

wherein:

$R^5$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^5$ is optionally substituted with $C_1$ to $C_4$ alkyl, $C_1$ to $C_4$ alkenyl, $C_1$ to $C_4$ alkoxy, —OH, —SH and —$CO_2R^7$, cycloalkyl, cycloalkenyl, heterocyclic alkyl, alkaryl, heteroaryl, heteroalkaryl, or any combination thereof;

$R^7$ is hydrogen, $C_1$ to $C_4$ alkyl or $C_1$ to $C_4$ alkenyl;

$R^5$ is optionally interrupted by oxygen, nitrogen, sulfur or any combination thereof; and $R^6$ is hydrogen, $C_1$ to $C_4$ alkyl or $C_1$ to $C_4$ alkenyl.

Special mention is also made of those having the formula

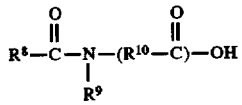     III wherein: $R^8$ is (i) $C_3$–$C_{10}$ cycloalkyl, optionally substituted with $C_1$–$C_7$ alkyl, $C_2$–$C_7$ alkenyl, $C_1$–$C_7$ alkoxy, hydroxy, phenyl, phenoxy or —$CO_2R^{11}$, wherein $R^{11}$ is hydrogen, $C_1$–$C_4$ alkyl, or $C_2$–$C_4$ alkenyl; or (ii) $C_1$–$C_6$ alkyl substituted with $C_3$–$C_{10}$ cycloalkyl;

$R^9$ is hydrogen, $C_1$–$C_4$ alkyl, or $C_2$–$C_4$ alkenyl;

$R^{10}$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$ alkyl), phenyl ($C_2$–$C_{10}$ alkenyl), naphthyl ($C_1$–$C_{10}$ alkyl) or naphthyl ($C_2$–$C_{10}$ alkenyl);

$R^{10}$ being optionally substituted with $C_1$–$C_4$ alkyl, $C_2$–$C_4$ alkenyl, $C_1$–$C_4$ alkoxy, —OH, —SH, —$CO_2R^{12}$, $C_3$–$C_{10}$ cycloalkyl, $C_3$–$C_{10}$ cycloalkenyl, heterocyclic having 3–10 ring atoms wherein the hetero atom is one or more of N, O, S or any combination thereof, aryl, ($C_1$–$C_{10}$ alk)aryl, ar($C_1$–$C_{10}$ alkyl), or any combination thereof;

$R_{10}$ being optionally interrupted by oxygen, nitrogen, sulfur, or any combination thereof; and $R^{12}$ is hydrogen, $C_1$–$C_4$ alkyl, or $C_2$–$C_4$ alkenyl.
Some preferred acylated amino acids include salicyloyl phenylalanine, and the compounds having the formulas:
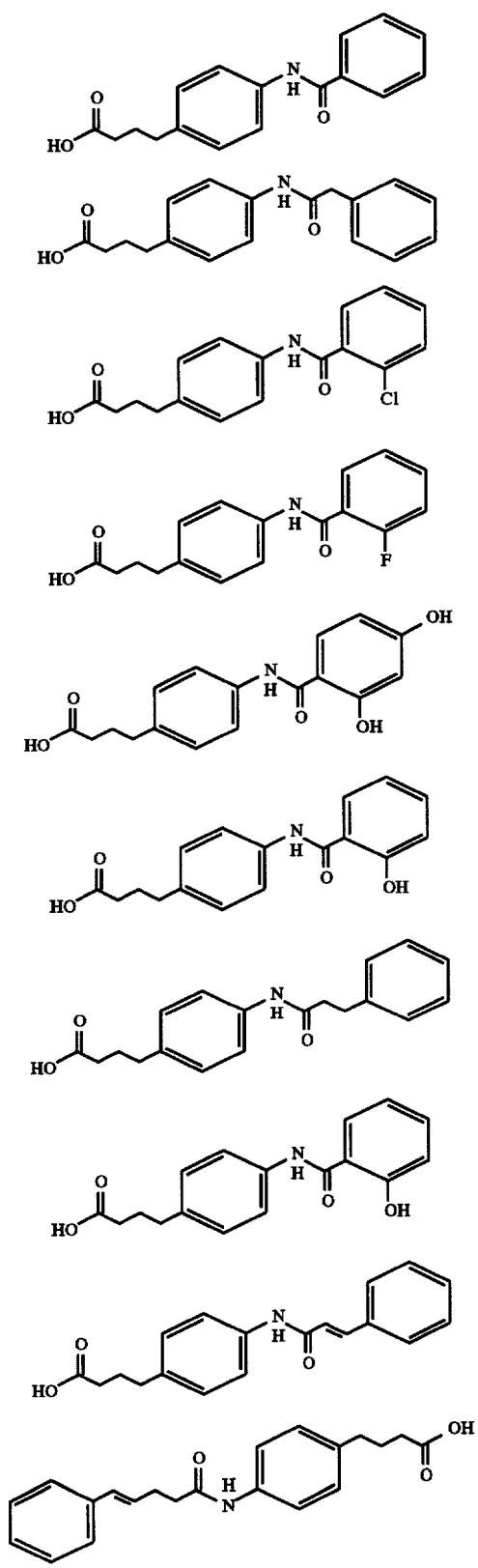
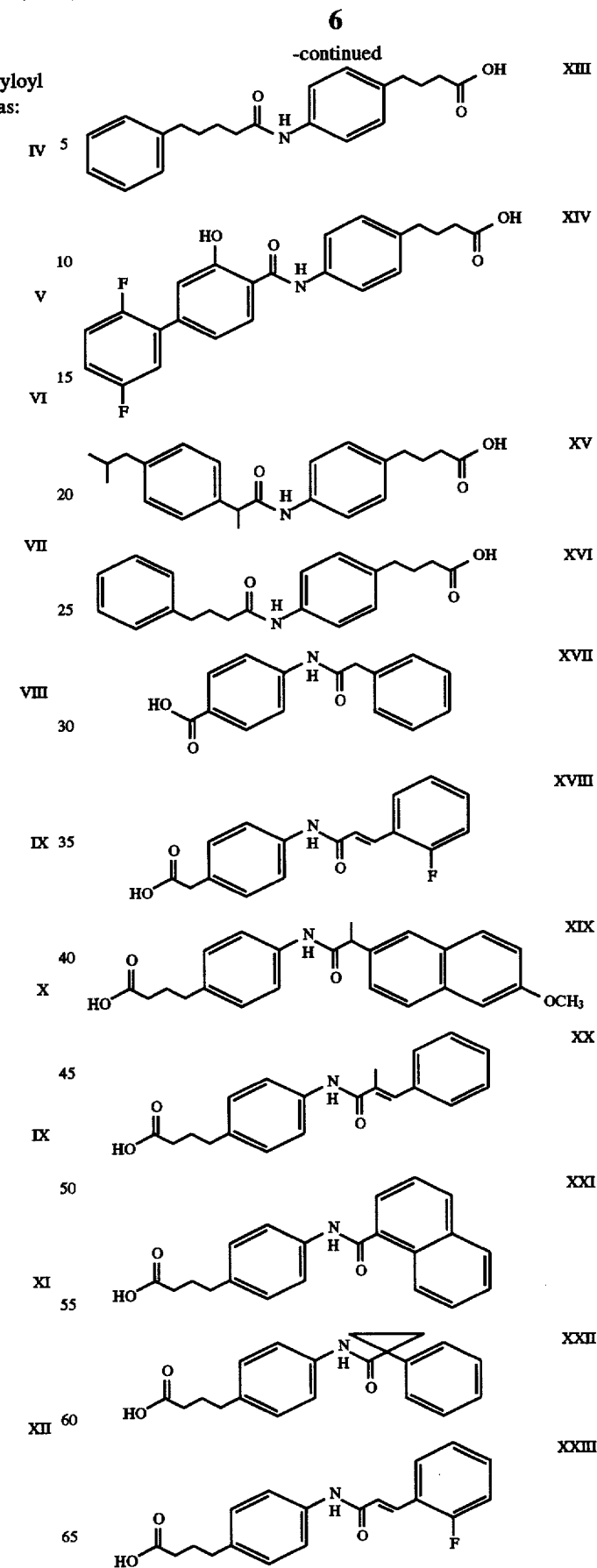

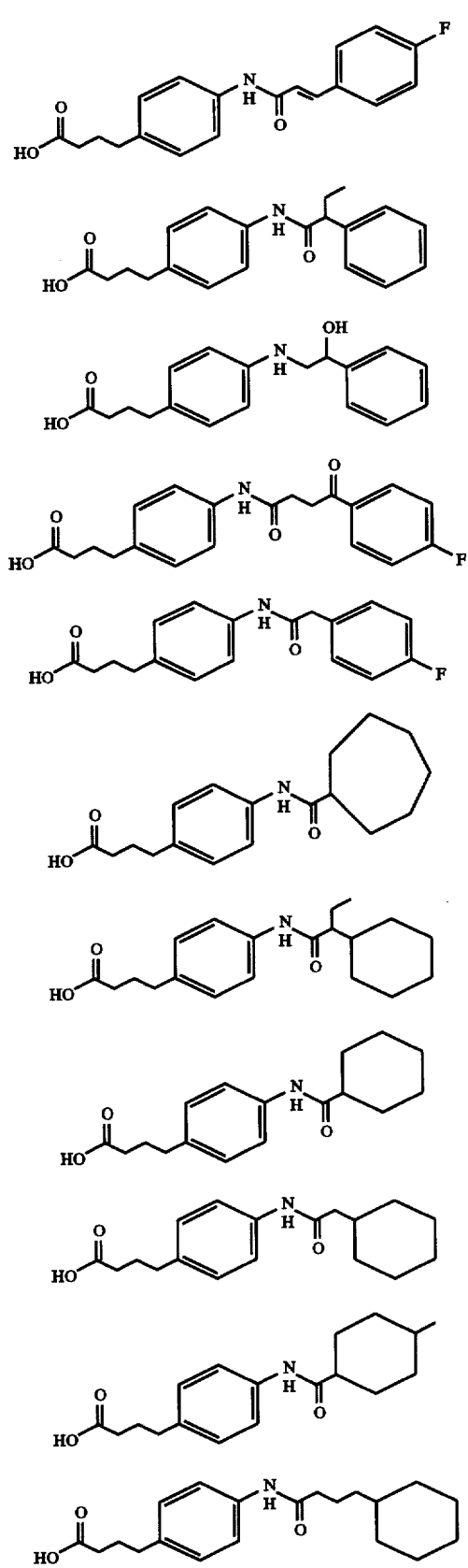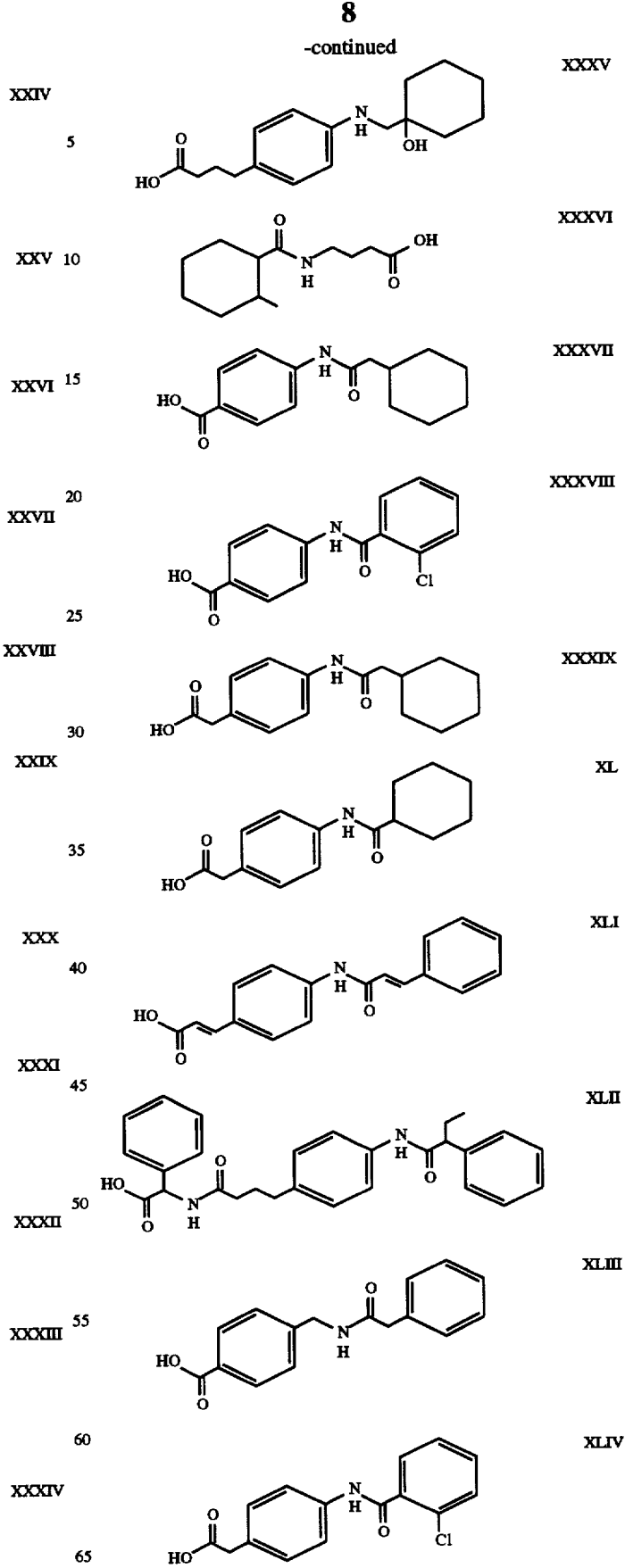

-continued

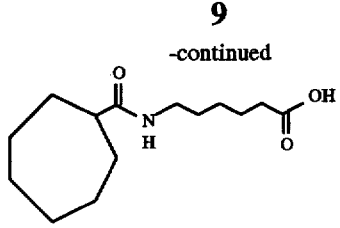

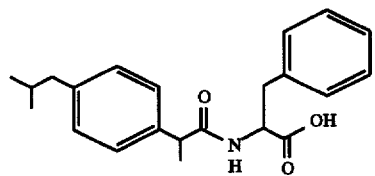

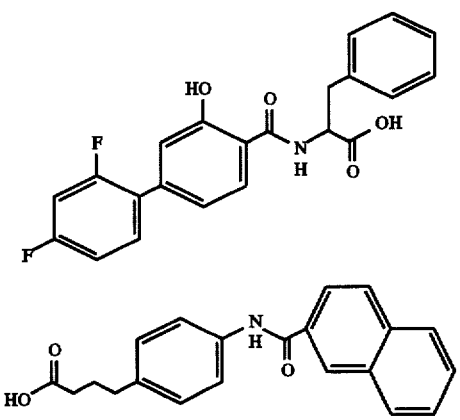

Special mention is made of compounds having the formula:

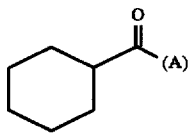 XLIX wherein A is Tyr, Leu, Arg, Trp, or Cit; and optionally wherein if A is Tyr, Arg, Trp or Cit; A is acylated at 2 or more functional groups.

Preferred compounds are those wherein A is Tyr; A is Tyr and is acylated at 2 functional groups; A is Leu; A is Arg; A is Arg and is acylated at 2 functional groups; A is Trp; A is Trp and is acylated at 2 functional groups; A is Cit; and A is Cit and is acylated at 2 functional groups.

Special mention is also made of compounds having the formula:

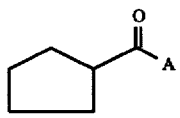 L wherein A is Arg or Leu; and wherein if A is Arg, A is optionally acylated at 2 or more functional groups;

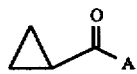 LI where A is Leu or phenylglycine;

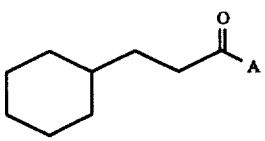 LII wherein A is phenylglycine; and

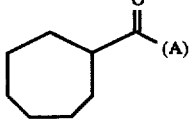 LIII wherein A is phenylglycine.

Acylated amino acids may be prepared by reacting single amino acids, mixtures of two or more amino acids, or amino acid esters with an amine modifying agent which reacts with free amino moieties present in the amino acids to form amides.

Suitable, but non-limiting, examples of acylating agents useful in preparing acylated amino acids include acid chloride acylating agents having the formula

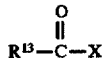

wherein:

$R^{13}$ an appropriate group for the modified amino acid being prepared, such as, but not limited to, alkyl, alkenyl, cycloalkyl, or aromatic, and particularly methyl, ethyl, cyclohexyl, cyclophenyl, phenyl, or benzyl, and X is a leaving group. Typical leaving groups include, but are not limited to, halogens such as chlorine, bromine and iodine.

Examples of the acylating agents include, but are not limited to, acyl halides including, but not limited to, acetyl chloride, propyl chloride, cyclohexanoyl chloride, cyclopentanoyl chloride, and cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. Preferred acylating agents include benzoyl chloride, hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as the carbodiimide derivatives of amino acids, particularly hydrophilic amino acids such as phenylalanine, tryptophan, and tyrosine. Further examples include dicyclohexylcarbodiimide and the like.

If the amino acid is multifunctional, i.e., has more than one —OH, —NH$_2$ or —SH group, then it may optionally be acylated at one or more functional groups to form, for example, an ester, amide, or thioester linkage.

For example, in the preparation of many acylated amino acids, the amino acids are dissolved in an aqueous alkaline solution of a metal hydroxide, e.g., sodium or potassium hydroxide and the acylating agent added. The reaction time can range from about 1 hour to about 4 hours, preferably about 2 to about 2.5 hours. The temperature of the mixture is maintained at a temperature generally ranging between about 5° C. and about 70° C., preferably between about 10° C. and about 50° C. The amount of alkali employed per equivalent of NH$_2$ groups in the amino acids generally ranges between about 1.25 moles and about 3 moles, and is preferably between about 1.5 moles and about 2.25 moles per equivalent of $NH_2$. The pH of the reaction solution generally ranges between about pH 8 and about pH 13, and is preferably between about pH 10 and about pH 12. The amount of amino modifying agent employed in relation to the quantity of amino acids is based on the moles of total free $NH_2$ in the amino acids. In general, the amino modifying agent is employed in an amount ranging between about 0.5 and about 2.5 mole equivalents, preferably between about 0.75 and about 1.25 equivalents, per molar equivalent of total $NH_2$ groups in the amino acids.

The modified amino acid formation reaction is typically quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and modified amino acids are collected by filtration or decantation. The crude modified amino acids are then mixed with water. Insoluble materials are removed by filtration, and the filtrate is dried in vacuo. The yield of modified amino acids generally ranges between about 30 and about 60%, and usually about 45%. The present invention also contemplates amino acids which have been modified by multiple acylation, e.g., diacylation, triacylation, etc.

If amino acid esters or amides are the starting materials, they are dissolved in a suitable organic solvent such as dimethylformamide or pyridine, and are reacted with the amino modifying agent at a temperature ranging between about 5° C. and about 70° C., preferably about 25° C., for a period ranging between about 7 and about 24 hours. The amount of amino modifying agents used relative to the amino acid esters are the same as described above for amino acids.

Thereafter, the reaction solvent is removed under negative pressure, and optionally, the ester or amide functionality can be removed by hydrolyzing the modified amino acid ester with a suitable alkaline solution, e.g., 1N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g., with an aqueous 25% hydrochloric acid solution, to a pH ranging between about 2 and about 2.5. The modified amino acid precipitates out of solution and is recovered by conventional means such as filtration or decantation.

The modified amino acids may be purified by acid precipitation, recrystallization, or fractionation on solid column supports. Fractionation may be performed on a suitable solid column supports such as silica gel or alumina, using solvent mixtures such as acetic acid/butanol/water as the mobile phase; reverse phase column supports using trifluoroacetic acid/acetonitrile mixtures as the mobile phase; and ion exchange chromatography using water as the mobile phase. The modified amino acids may also be purified by extraction with a lower alcohol such as methanol, butanol, or isopropanol to remove impurities such as inorganic salts.

The modified amino acids generally are soluble in alkaline aqueous solution ($pH \geq 9.0$); partially soluble in ethanol, n-butanol and 1:1 (v/v) toluene/ethanol solution; and insoluble in neutral water. The alkali metal salts, e.g., the sodium salts of the modified amino acids, are generally soluble in water at about a pH of 6–8.

In poly amino acids or peptides, one or more of the amino acids may be modified (acylated). Modified poly amino acids and peptides may include one or more acylated amino acid(s). Although linear modified poly amino acids and peptides will generally include only one acylated amino acid, other poly amino acid and peptide configurations can include more than one acylated amino acid. Poly amino acids and peptides can be polymerized with the acylated amino acid(s) or can be acylated after polymerization.

Special mention is made of the compound:

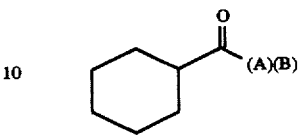

wherein A and B independently are Arg or Leu.

Sulfonated Amino Acids

Sulfonated modified amino acids, poly amino acids, and peptides are modified by sulfonating at least one free amine group with a sulfonating agent which reacts with at least one of the free amine groups present.

Special mention is made of compounds of the formula

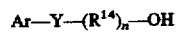

wherein Ar is a substituted or unsubstituted phenyl or naphthyl;
Y is $—SO_2—$, $R^{14}$ has the formula

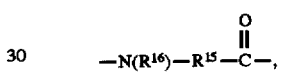

wherein:
$R^{15}$ is $C_1$ $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);
$R^{15}$ is optionally substituted with $C_1$ to $C_4$ alkyl, $C_1$ to $C_4$ alkenyl, $C_1$ to $C_4$ alkoxy, $—OH$, $—SH$ and $—CO_2R^{17}$ or any combination thereof;
$R^{17}$ is hydrogen, $C_1$ to $C_4$ alkyl or $C_1$ to $C_4$ alkenyl;
$R^{15}$ is optionally interrupted by oxygen, nitrogen, sulfur or any combination thereof; and
$R^{16}$ is hydrogen, $C_1$ to $C_4$ alkyl or $C_1$ to $C_4$ alkenyl.

Suitable, but non-limiting, examples of sulfonating agents useful in preparing sulfonated amino acids include sulfonating agents having the formula $R^{18}—SO_2—X$ wherein $R^{18}$ is an appropriate group for the modified amino acid being prepared such as, but not limited to, alkyl, alkenyl, cycloalkyl, or aromatics and X is a leaving group as described above. One example of a sulfonating agent is benzene sulfonyl chloride.

Modified poly amino acids and peptides may include one or more sulfonated amino acid(s). Although linear modified poly amino acids and peptides used generally include only one sulfonated amino acid, other poly amino acid and peptide configurations can include more than one sulfonated amino acid. Poly amino acids and peptides can be polymerized with the sulfonated amino acid(s) or can be sulfonated after polymerization.

Delivery Systems

In one embodiment of the present invention, the modified amino acids, poly amino acids, or peptides may be used directly as a carrier by simply mixing one or more modified amino acids, poly amino acids, or peptides with the antigen prior to administration. In another embodiment, the modified amino acids may be used to form microspheres containing the antigen. Delivery of an antigen and a carrier as described herein results in enhanced immune responses. This latter advantage is particularly found in the microsphere form.

Microspheres containing antigen can generally be of the matrix form or the microcapsule form. The matrix form includes both a hollow matrix sphere in which the carrier forms a matrix shell around a hollow center and the active agent is distributed throughout the matrix and a solid matrix sphere in which the carrier forms a spherical matrix continuum in which the active agent is distributed.

The microcapsule form is one in which the encapsulated active agent either is in solution or is a solid, with the carrier forming a shell around the encapsulated material. The microcapsule form is the form most often taken by the self assembly of the carriers of the present invention.

If the delivery composition is to be of the microsphere form, carrier microspheres can be prepared by dissolving the carrier in an appropriate solute and then stimulating self assembly by contacting the carrier solution with a precipitator. Solubility of the carrier can be regulated by the selection of the appropriate amino acids.

Furthermore, the microsphere carriers, and therefore, the compositions of the present invention can be pH adapted to be selectively soluble in specific acidic, basic, or neutral pH ranges.

Compositions which are targeted to an acidic environment can be made selectively soluble at acidic pH, such as the pH in the stomach. These compositions are prepared with an acid-soluble carrier. The acid-soluble carrier exists largely in the cation form in at least a portion of the pH range from about 1 to about 6.8. However, above about 6.8 or at selected ranges above pH 6.8, the carrier is largely unprotonated and insoluble in water. Therefore, the carrier could self assemble to microspheres at basic or neutral pH, and the active agent in the delivery composition would not be released until the carrier solubilizes upon encountering an acidic pH.

Compositions which are to be targeted to an alkaline environment can be made selectively soluble at alkaline pH, such as the pH in the distal portion of the intestine. These compositions are prepared with a base-soluble carrier. The base-soluble carrier exists largely in an anionic form in at least a portion of the pH range of from about 7.2 to about 11. However, below and at pH 7.2, the carrier is largely protonated and insoluble in water. Therefore, the carrier could self assemble to microspheres at acidic or neutral pH, and the antigen in the delivery composition would not be released until the carrier solubilizes upon encountering a basic pH.

Compositions which are targeted to a neutral environment can be made selectively soluble at neutral pH. These compositions are prepared with a neutral-soluble carrier. The neutral-soluble carrier exists largely in a neutral form at neutral pH, i.e. from about 6.8 to about 7.2. However, above or below this range, the carrier is insoluble in water. Therefore, the carrier could self assemble to microspheres at acidic or basic pH, and the antigen in the delivery composition would not be released until the carrier solubilizes upon encountering a neutral pH.

In a typical microsphere formulation, the final solution can contain from about 10 mg to about 2000 mg of carrier per ml of solution, preferably between about 75 to about 500 mg of carrier per ml of solution, and most preferably from about 75 to about 200 mg per ml. Optionally, the mixture is heated to a temperature between about 20° C. and about 60° C., preferably about 40° C., until the carrier dissolves.

Particulates remaining in the solution may be filtered out by conventional means such as gravity filtration over filter paper. The carrier solution usually is maintained at the elevated temperature and is mixed with the antigen and a precipitator, for example, an acid solution such as, for example, aqueous acetic or citric acid at a concentration ranging from about 1N to about 3N for acid insoluble carriers, a basic solution for base insoluble carriers, and a neutralizing solution for neutral insoluble carriers. The antigen can be mixed with the precipitating solution or can be used separately. The resultant mixture is maintained for a period of time sufficient for microsphere formation as observed by light microscopy. Although it is preferred that the carrier solution is added to the precipitating solution, the precipitating solution can be added to the carrier solution as well.

The solutions above may optionally contain additives such as stabilizing additives. The presence of such additives promotes the stability and dispersability of the active agent in solution. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, polylysine, and cyclodextrins. The preferred stabilizing agents are gum acacia, gelatin, and methyl cellulose.

The amount of antigen which may be encapsulated by the microsphere is dependent upon a number of factors which include the concentrations of antigen in the encapsulating solution as well as their affinities for the carrier. The concentrations of antigen in the final formulation also will vary depending on the required dosage of administration. When necessary, the exact concentrations can be determined by, for example, reverse phase HPLC analysis.

When the present compositions are in microsphere form, the particle size of the microsphere can also aid in providing efficient delivery of the antigen to the target. Typically, microspheres of the present invention will have a diameter of less than 10 µm, preferably in the range of from about 0.1 µm to about 10 µm, and most preferably in the range of from 0.2 µm to about 10 µm. The size of the microspheres containing an antigen can be controlled by manipulating a variety of physical or chemical parameters, such as pH, osmolarity, ionic strength of the encapsulating solution, or size of the ions in solution, and/or by the choice of the precipitator used in the microsphere forming and loading process.

For example, in the GI tract, it is often desirable to use microspheres which are sufficiently small to deliver effectively the antigen to the targeted area within the gastrointestinal tract. Small microspheres can also be administered parenterally by suspending the spheres in an appropriate fluid (e.g. isotonic solution) and injecting the solution directly into the circulatory system intramuscularly or subcutaneously. The mode of administration of the delivery compositions will vary, of course, depending upon the requirement of the antigen administered. It has been noted that large amino acid microspheres (greater than 50 µm) tend to be less effective as oral delivery systems.

The compositions of the present invention may also include one or more enzyme inhibitors. Such enzyme inhibitors include, but are not limited to, compounds such as actinonin or epiactinonin and derivatives thereof. These compounds have the formulas below:

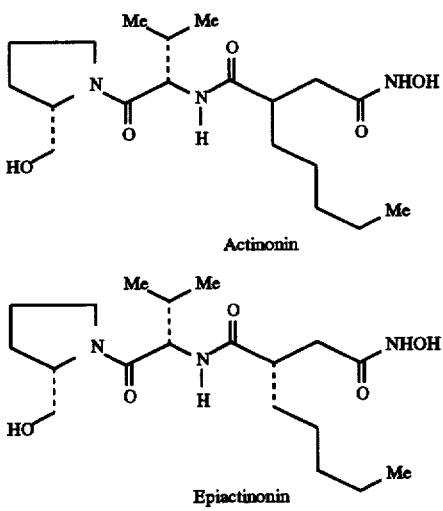

Actinonin

Epiactinonin

Derivatives of these compounds are disclosed in U.S. Pat. No. 5,206,384. Actinonin derivatives have the formula:

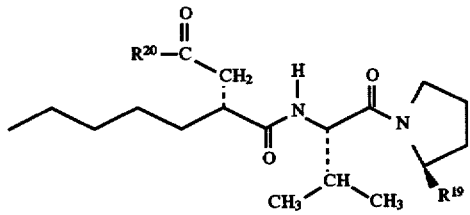

wherein $R^{19}$ is sulfoxymethyl or carboxyl or a substituted carboxy group selected from carboxamide, hydroxyaminocarbonyl and alkoxycarbonyl groups; and $R^{20}$ is hydroxyl, alkoxy, hydroxyamino or sulfoxyamino group. Other enzyme inhibitors include, but are not limited to, aprotinin (Trasylol) and Bowman-Birk inhibitor.

The compositions of the present invention may be formulated into dosage units by the addition of one or more excipient(s), diluent(s), disintegrant(s), lubricant(s), plasticizer(s), colorant(s), or dosing vehicle(s). Preferred dosage unit forms are oral dosage unit forms. Most preferred dosage unit forms include, but are not limited to, tablets, capsules, or liquids. The dosage unit forms can include biologically or immunogenically effective amounts of the antigen but can include less than such an amount if multiple dosage unit forms are to be used to administer a total dosage of the antigen. Dosage unit forms are prepared by methods conventional in the art. These amounts can also vary according to whether the dosage is to be used as a prime or booster.

The carriers of the present invention do not alter the physiological and biological properties of the antigen. Furthermore, the encapsulation process need not alter the structure of the antigen. Any antigen can be incorporated within the amino acid microspheres.

The compositions are particularly advantageous for oral vaccination or immunization with antigens which otherwise would be destroyed or rendered less effective by conditions encountered within the body of the animal to which it is administered, before the microsphere reaches its target zone. For example, peptide or protein antigens, which, by themselves, do not pass or are not taken up in the gastrointestinal mucosa and/or are susceptible to chemical cleavage by acids and enzymes in the gastrointestinal tract can be delivered. Such antigens further include, for example, those used to provide immunization against diseases including but not limited to, influenza, diphtheria, tetanus, measles, polio, hepatitis and the like. The compositions of the invention are more effective at inducing both mucosal and serum antibody responses than antigens which are administered without the carriers specified herein. The antigens are administered to a mammal for their biological effect, such as, for example as immune stimulators.

Administration of the present compositions or dosage unit forms preferably is oral or by subcutaneous or intraduodenal injection.

DESCRIPTION OF THE PREFERRED EMBODIMENTS

The following examples illustrate the invention without limitation.

EXAMPLE 1

PREPARATION OF N-CYCLOHEXANOYL-(L)-TYROSINE.

(L)-Tyrosine (61.6 g., 0.34 mole) was dissolved in 190 mL of 2N sodium hydroxide. Cyclohexanoyl chloride (49.32 mL, 0.34 mole) was added dropwise to the mixture. Additional aqueous 2N sodium hydroxide was added and the reaction mixture was allowed to stir at room temperature for 2 hours. The mixture was then acidified to pH 9.5 with aqueous (4:1) hydrochloric acid. A precipitate formed which was separated by vacuum filtration. The solids were dissolved in 2N sodium hydroxide and dried by lyophilization to furnish 33.5 g of N,O-dicyclohexanoyl-(L)-tyrosine. The product was purified by column chromatography on silica gel using butanol/acetic acid/water as the eluent system. The pure product was a white solid.

1. Mass Spectrum: M+23 m/e 314.

2. $^1$H NMR (300 MHz,DMSO-d6): d=6.8 (d, 2 H); 6.4 (d,2 H); 4.4 (m, 1 H); 2.5 (ddd,2 H); 2.0 (m,2 H); 1.6 (m,10 H); 1.2 (m, 10 H).

3. IR (KBr) cm–1: 3350, 2900, 2850, 1600, 1520, 1450, 1400, 1300.

EXAMPLE 2

PREPARATION OF N-CYCLOHEXANOYL-(L)-ARGININE (L)-Arginine (103.2 g., 0.6 mole) was dissolved in 600 mL of 2N sodium hydroxide. Cyclohexanoyl chloride (87 mL, 0.6 mole) was added dropwise to the mixture. The reaction mixture was maintained at 50° C. for 2 hours. The mixture was then cooled to room temperature and acidified to pH 2.3 with aqueous (4:1) hydrochloric acid. The precipitate which formed was separated by decantation. The solids were dissolved in 2N sodium hydroxide and dried by lyophilization to furnish 64.1 g of crude N-cyclohexanoyl-(L)-arginine. The product was purified by column chromatography on silica gel/using butanol/acetic acid/water as the eluent system. The products isolated were N-cyclohexanoyl-(L)-arginine and N($\alpha$)-N($\epsilon$)-dicyclohexanoyl-(L)-arginine.

N-cyclohexanoyl-(L)-arginine

1. Mass Spectrum: M+1 m/e 395.

2. $^1$H NMR (300 MHz, DMSO-d6): ppm $\delta$=8.75 (br, 1 H); 7.6 (br, 5 H); 4.0 (m, 1 H); 3.05 (m, 2 H); 2.15 (m, 1 H); 1.1–1.5 (br.m, 14 H).

N($\alpha$),N($\epsilon$)-dicyclohexanoyl-(L)-arginine

1. Mass Spectrum: M+1 m/e 285.

2. $^1$H NMR: (300 MHz, DMSO-d6): d=2.0 (m, 3 H); 1.8–1.4 (br. m, 17 H); 1.3–1.0 (br. m, 20 H)

EXAMPLE 3

PREPARATION OF N-CYCLOHEXANOYL-(L)-CITRULLINE

L-Citrulline (35.2 g., 0.2 mole) was dissolved in 200 mL of 2N sodium hydroxide. Cyclohexanoyl chloride (29 mL, 0.2 mole) was added dropwise to the mixture. The reaction mixture was maintained at about 25° C. for 1 hour. The mixture was then acidified to pH 2.6 with aqueous (4:1) hydrochloric acid. The precipitate which formed was separated by decantation. The solids were dissolved in 2N sodium hydroxide to pH 6.5 and dried by lyophilization to furnish 44.2 g of N-cyclohexanoyl-(L)-citrulline. The product was a white solid.

1. Mass Spectrum: M+23 m/e 308.
2. $^1$H NMR (300 MHz,DMSO-d6): d=4.1 (dd, 1 H); 2.9 (t, 2 H); 2.1 (m,2 H); 1.6–1.2 (br.m, 14 H).
3. IR (KBr) cm−1: 3400, 3300, 2950, 2850, 1700, 1650, 1600, 1450, 1400 cm−1.

EXAMPLE 4

PREPARATION OF N-CYCLOPENTANOYL-(L)-ARGININE (L)-Arginine (32.8 g., 0.19 moles) was dissolved in 188 mL of 2N sodium hydroxide. Cyclopentanoyl chloride (22.9 mL, 0.19 moles) were added dropwise to the mixture. The reaction mixture was maintained at about 25° C. for 2 hours. The mixture was then acidified to pH 1.5 with aqueous (4:1) hydrochloric acid. The precipitate which formed was separated by decantation. The solids were dissolved in 2N sodium hydroxide to pH 7.5 and dried by lyophilization to furnish 67.4 g of N-cyclopentanoyl-(L)-arginine. The product was a white solid. Mass Spectrum: M+1 m/e 271.

EXAMPLE 5

PREPARATION OF N-CYCLOHEXANOYL-(t)-ARGININE (t)-Arginine (14.2 g., 0.1 mole) was dissolved in 100 mL of 2N sodium hydroxide. Cyclohexanoyl chloride (13 mL, 0.098 mole) was added dropwise to the mixture. The reaction mixture was maintained at 25° C. for 2 hours. The mixture was then cooled to room temperature and acidified to pH 6.6 with aqueous (4:1) hydrochloric acid. The white precipitate which formed was separated by decantation. The solids were dissolved in a minimum of 2N sodium hydroxide. The product, a white solid, (11.6 g, 49%) was isolated by lowering the pH of the purified by acidification with aqueous (4:1) hydrochloric acid to a pH of about 7–9.

1. Mass Spectrum: M+1 m/e 2423
2. $^1$H NMR (300 MHz, D$_2$O): ppm δ=4.9 (s, 1 H); 2.2 (m, 1 H); 1.7–1.4 (m, 5 H); 1.3–1.0 (m, 5 H); 0.8 (s, 9 H).
3. IR (KBr) cm−1: 3350, 2950, 2850, 1550, 1500, 1400 cm$^{-1}$ Following the procedure of Examples 1–5 the following amino acids and peptides have been synthesized:

cyclohexanoyl-Ala, m-(cyclohexanolyamino)benzoic acid, p-(cyclohexanoylamino)benzoic acid, 4-(cyclohexanoyl-amino)butyric acid, 6-(cyclohexanoylamino)hexanoic acid, cyclohexanoylanthranilic acid, cyclohexanoyl-Arg-Leu, cyclohexanoyl-Asp, isatoicanhydride-Asp, cyclohexanoyl-Glu, cyclohexanoyl-Gly, cyclohexanoyl-Gly-Arg, cyclohexanoyl-Ile, cyclohexanoyl-Leu, cyclopentanoyl-Leu, cyclopropanoyl-Leu, 3-methycyclohexanoyl-Leu, 2-methycyclohexanoyl-Leu, 4-methycyclohexanoyl-Leu, cyclohexanoyl-(D)-Leu, cyclohexanoyl-(t)-Leu, cyclohexanoyl-Leu-Arg, cyclohexanoyl-Leu-Leu, cyclohexanoyl-(D)-Leu-(L)-Leu, cyclohexanoyl-Leu-Lys-Val, cyclohexanoyl-Lys, cyclohexanoyl-Orn, cyclohexanoyl-Phe, cycloheptanoyl-Phg, cyclohexylpropanoyl-Phg, cyclohexanoyl-Phg, cyclopentanoyl-Phg, cyclopropanoyl-Phg, 4-methycyclohexanoyl-Phg, cyclohexanoyl-(D)-Phg, cyclohexanoyl-Tio, cyclohexanoyl-Trp, cyclohexanoyl-Tyr-Leu, cyclohexanoyl-Val, cyclopentanoyl-Val, cyclohexanoyl-Val-Val, cycloheptanoyl-Leu, and cyclohexylpropanoyl-Leu.

EXAMPLE 6

PREPARATION OF SULFONATED 4-(4-AMINOPHENYL)BUTYRIC ACID 4-(4-Aminophenyl)butyric acid, (20 g 0.11 moles) was dissolved in 110 mL of aqueous 2N sodium hydroxide solution. After stirring for about 5 minutes at room temperature, benzene sulfonyl chloride (14.2 mL, 0.11 moles) was added dropwise into the amino acid solution over a 15 minute period. After stirring for about 3 hours at room temperature the mixture was acidified to pH 2 by addition of hydrochloric acid. This furnished a light brown precipitate which was isolated by filtration. The precipitate was washed with warm water and dried. The yield of 4-(phenylsulfonamido)4-phenylbutyric acid was 24.3 g (69%). The melting point was 123–25° C.

If necessary, the modified amino acids can be purified by recrystallization and/or chromatography.

EXAMPLE 7

PREPARATION OF SULFONATED 4-AMINOBENZOIC ACID

Following the procedure of Example 6 4-aminobenzoic acid was converted to 4-(phenylsulfonamido)benzoic acid.

EXAMPLE 8

PREPARATION OF SULFONATED 4-AMINOPHENYLACETIC ACID, 4-AMINOHIPPURIC ACID, AND 4-AMINOMETHYLBENZOIC ACID

Following the procedure of Example 6, 4-aminophenylacetic acid, 4-aminohippuric acid, and 4-aminomethylbenzoic acid were converted to 4-(phenylsulfonamido)phenylacetic acid, 4-(phenylsulfonamido)hippuric acid, and 4-(phenylsulfonamidomethyl)benzoic acid respectively.

EXAMPLE 9

PREPARATION OF A MIXTURE OF SULFONATED AMINO ACIDS

A mixture of sixteen amino acids were prepared prior to reaction. The constituents of the mixture are summarized in Table 1. 65 grams of the amino acid mixture (total concentration of [—NH$_2$] groups=0.61 moles) was dissolved in 760 mL of 1N sodium hydroxide solution (0.7625 equivalents) at room temperature. After stirring for 20 minutes, benzene sulfonyl chloride (78 ml, 1 eq.) was added over a 20 minute period. The reaction mixture was then stirred for 2.5 hours, without heating. As some precipitation had occurred, additional NaOH solution (2N) was added to the solution until it reached pH 9.3. The reaction mixture stirred overnight at room temperature. Thereafter, the mixture was acidified using dilute hydrochloric acid (38%, 1:4) and a cream colored material precipitated out. The resulting precipitate was isolated by decantation and dissolved in sodium hydroxide (2N). This solution was then reduced in vacuo to give a yellow solid, which was dried on the lyophilizer.

TABLE 1

Amino Acid Composition

| Amino Acid | Weight (g) | % of Total Weight | No. of moles of each Amino Acid ($\times 10^{-2}$) | No. of Moles of [—$NH_2$] |
|---|---|---|---|---|
| Thr | 2.47 | 3.8 | 2.07 | 2.07 |
| Ser | 2.25 | 3.46 | 2.1 | 2.1 |
| Ala | 4.61 | 7.1 | 5.17 | 5.17 |
| Val | 4.39 | 6.76 | 3.75 | 3.75 |
| Met | 0.53 | 0.82 | 0.35 | 0.35 |
| Ile | 2.47 | 3.8 | 0.36 | 0.36 |
| Leu | 3.86 | 5.94 | 2.95 | 2.95 |
| Tyr | 1.03 | 1.58 | 0.56 | 0.56 |
| Phe | 4.39 | 6.76 | 0.27 | 0.27 |
| His | 2.47 | 3.8 | 1.6 | 3.2 |
| Lys | 4.94 | 7.6 | 3.4 | 6.8 |
| Arg | 5.13 | 7.9 | 2.95 | 5.90 |
| Glutamine | 9.87 | 15.18 | 6.76 | 13.42 |
| Glutamic Acid | 9.87 | 15.18 | 6.70 | 6.70 |
| Asparagine | 3.32 | 5.11 | 2.51 | 5.02 |
| Aspartic Acid | 3.32 | 5.11 | 2.50 | 2.50 |

EXAMPLE 10

PREPARATION OF A MIXTURE OF SULFONATED AMINO ACIDS

An 86.1 g (0.85 moles of $NH_2$) mixture of amino acids (see Table 2) was dissolved in 643 mL (1.5 eq.) of aqueous 2N sodium hydroxide solution. After stirring for 30 minutes at room temperature, benzene sulfonyl chloride (108 mL, 0.86 moles) was added portionwise into the amino acid solution over a 15 minute period. After stirring for 2.5 hours at room temperature, the pH of the reaction mixture (pH 5) was adjusted to pH 9 with additional 2N sodium hydroxide solution. The reaction mixture stirred overnight at room temperature. Thereafter, the pH of the reaction mixture was adjusted to pH 2.5 by addition of dilute aqueous hydrochloric acid solution (4:1, $H_2O:HCl$) and a precipitate of modified amino acids formed. The upper layer was discarded and the resulting yellow precipitate was isolated by decantation, washed with water and dissolved in 2N sodium hydroxide (2N). The solution was reduced in vacuo to give a yellow solid which was lyophilized overnight. The yield of crude modified amino acid was 137.9 g.

TABLE 2

| Amino Acid | Moles of Amino Acid ($\times 10^2$) | Moles of [—$NH_2$] $\times 10^{-2}$ |
|---|---|---|
| Valine | 7.5 | 7.5 |
| Leucine | 10.7 | 10.5 |
| Phenylalanine | 13.4 | 13.4 |

TABLE 2-continued

| Amino Acid | Moles of Amino Acid ($\times 10^2$) | Moles of [—$NH_2$] $\times 10^{-2}$ |
|---|---|---|
| Lysine | 21.0 | 42.0 |
| Arginine | 6.0 | 12.0 |

EXAMPLE 11

PREPARATION OF A MIXTURE OF MODIFIED AMINO ACIDS USING BENZOYL CHLORIDE

An 86 g (0.85 moles of $NH_2$) mixture of amino acids (see Table 2 in Example 10) was dissolved in 637 mL (1.5 eq.) of aqueous 2N sodium hydroxide solution. After stirring for 10 minutes at room temperature, benzoyl chloride (99 mL, 0.85 moles) was added portionwise into the amino acid solution over a 10 minute period. After stirring for 2.5 hours at room temperature, the pH of the reaction mixture (pH 12) was adjusted to pH 2.5 using dilute hydrochloric acid (4:1, $H_2O:HCl$) and a precipitate of modified amino acids formed. After settling for 1 hour, the resulting precipitate was isolated by decantation, washed with water and dissolved in sodium hydroxide (2N). This solution was then reduced in vacuo to give crude modified amino acids as a white solid (220.5 g).

EXAMPLE 12

PREPARATION OF SULFONATED L-VALINE

L-Valine (50 g, 0.43 mol) was dissolved in 376 mL (0.75 eq.) of aqueous 2N sodium hydroxide by stirring at room temperature for 10 minutes. Benzene sulfonyl chloride (68.7 mL, 0.38 mol, 1.25 eq.) was then added to the amino acid solution over a 20 minute period at room temperature. After stirring for 2 hours at room temperature, a precipitate appeared. The precipitate was dissolved by adding 200 mL of additional 2N sodium hydroxide solution. After stirring for an additional 30 minutes, dilute aqueous hydrochloric acid solution (4:1, $H_2O:HCl$) was added until the pH of the reaction mixture reached 2.6. A precipitate of modified amino acids formed and was recovered by decantation. This material was dissolved in 2N sodium hydroxide and dried in vacuo to give a white solid. Yield of crude modified amino acids=84.6 g, 77%).

EXAMPLE 13

PREPARATION OF MODIFIED PHENYLALANINE METHYL ESTER USING HIPPURYL CHLORIDE

L-Phenylalanine Methyl Ester Hydrochloride (15 g, 0.084 mole) was dissolved in dimethylformamide (DMF) (100 mL) and to this was added pyridine (30 mL). A solution of hippuryl chloride (16.6 g, 0084 moles in 100 mL DMF) was immediately added to the amino acid ester solution in two portions. The reaction mixture was stirred at room temperature overnight. The reaction mixture was then reduced in vacuo and dissolved in 1N aqueous sodium hydroxide. The solution was heated at 70° C. for 3 hours in order to hydrolyze the methyl ester to a free carboxyl group. Thereafter, the solution was acidified to pH 2.25 using dilute aqueous hydrochloric acid solution (1:3 $HCl/H_2O$). A gum-like precipitate formed and this was recovered and dissolved in 1N sodium hydroxide. The solution was reduced in vacuo to afford 18.6 g of crude modified amino acid product (Yield 18.6 g). After recrystallization from acetonitrile, pure modified phenylalanine (12 g) was recovered as a white powder. m.p. 223°–225° C.

EXAMPLE 14

PREPARATION OF ANTIGEN/CARRIER COMPOSITIONS

A carrier solution was prepared by adding 900 mg of N-cyclohexanoyl-(I)-tyrosine and 1.35 g of N-cyclohexanoylleucine to 1.5 ml of water.

An antigen solution was prepared by adding 3 mg of Ovalbumin (OVA) antigen to 1.5 ml of a solution of 1.7N citric acid/1% gum acacia/2% cyclodextrin.

The carrier solution and the OVA antigen solution were warmed to 40° C. and mixed together. The sample had a carrier concentration of 75 mg/mL and an OVA antigen concentration of 1 mg/mL.

EXAMPLE 15

IMMUNE RESPONSE IN MICE

A standard CRPMI cell culture medium was prepared with the following ingredients:
1. MEM Amino Acid Solution (50*), (Gibco) (10 ml)
2. MEM Non-Essential Amino Acid Solution (10 ML 100X), (Gibco) (10 ml)
3. MEM Sodium Pyruvate (100 nM, 100*), (Gibco) (10 ml)
4. MEM Vitamin Solution (100*), (Gibco) (10 ml)
5. L-Glutamine (200 nM, 100*), (Gibco) (10 ml)
6. Penicillin-Streptomycin, (Gibco) (10 ml)
7. Gentamicin Reagent Solution (10 mg/ml), (Gibco) (1 ml)
8. Hepes Buffer Solution (1M), (Gibco) (2 ml)
9. 2-Mercaptoethanol (5×10M), (Sigma) (1 ml)
10. Sodium Bicarbonate, (Gibco) (2 g)
11. RPMI MEDIUM 1640, (Gibco) to make 1 liter.

For use as a washing medium, a 5% volume of FBS (Gemini Bioproducts Inc.) was added. For use as a culture medium, a 10% volume of FBS (Hyclone) was added.

Fasted mice were anesthetized with Ketamine, and then administered, by oral gavage, priming doses of antigen/carrier compositions prepared according to the method of Example 14 (0.1 mg OVA antigen and 7.5 mg of carrier). This procedure was repeated for three groups of mice according to the following schedule:
Group 1: Dosed on days 1, 2, 3, 8, 9, and 10.
Group 2: Dosed on days 8, 9, and 10.
Group 3: Dosed on day 10.
All groups were boosted with three consecutive daily doses eight weeks after the last priming dose of day 10.

After completion of the dosing procedures the mice were sacrificed. Their spleens were excised, and the spleen cells were obtained and prepared as follows:
1. Mince spleen with Forceps.
2. Lyse Red Blood Cells with 0.1M $NH_4Cl$-Tris (pH 7.1).
3. Wash spleen cells 3 times with CRPMI 5% FBS.
4. Resuspend spleen cells in CRPMI 10% FBS.
5. Count spleen cell density by Hemacytometer.
6. Adjust spleen cell density at $7 \times 10^6$/ml.

The spleen cells were assayed for OVA antigen specific T cell proliferation. The materials employed for the proliferation assay were as follows:

1. Flat bottom plate, 96 wells (Corning);
2. Thymidine, (methyl-3H)- (Dupont);
3. CVA (4 mg/ml in CRPMI);
4. mAbs-Anti-CD4 (GKL.5)—rat $IgG_1b$ (Hybridoma from ATCC); Anti-CD8(2.43)—Rat $IgG_2b$ (Hybridoma from ATCC).

The assay procedure was as follows:
1. Add 50 μl or 100 μl of spleen cell suspension to each well. ($7 \times 10^3$ cells/well)
2. Add OVA antigen solution or culture medium.
3. Add corresponding amount of mAb solution (40 μg/ml) or culture medium to total volume of 200 μl/well.
4. Incubate for 5 days in $CO_2$ incubator.
5. At one day before harvest, add 1 μCi/well of $^3$H-Thymidine.
6. Harvest cells and determine thymidine in a Beta counter.

Anti-CD4 antibodies or anti-CD8 antibodies were added to some wells to demonstrate that the proliferation was due to CD4+T cells.

Figure 2:
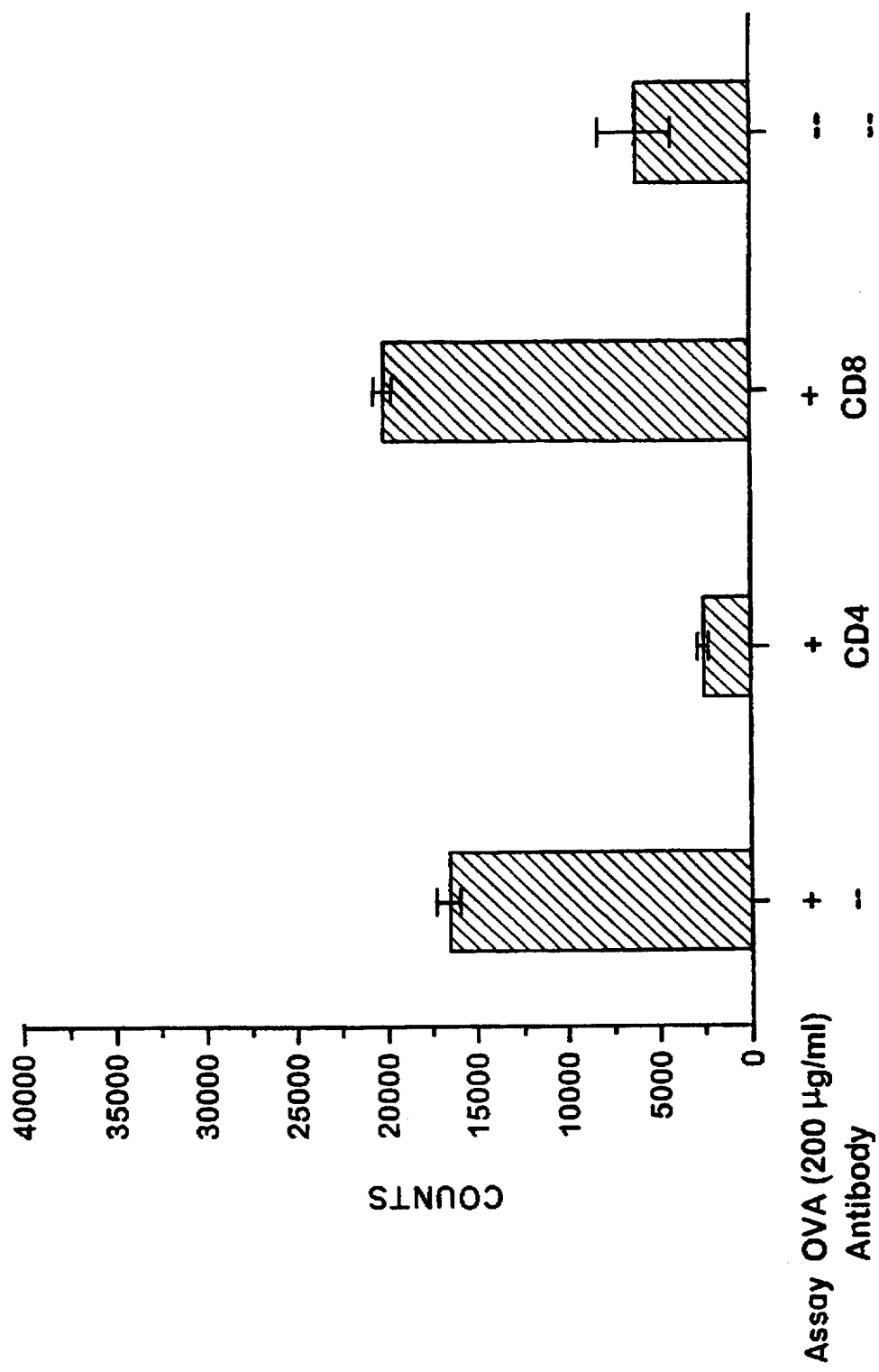
FIG. 2 is a graphic illustration of OVA antigen specific T cell proliferation after exposure to OVA antigen, of mouse spleen cells from mice dosed by oral gavage with OVA antigen and modified amino acid carrier. (Group 2 (6 priming doses)).
Figure 3:
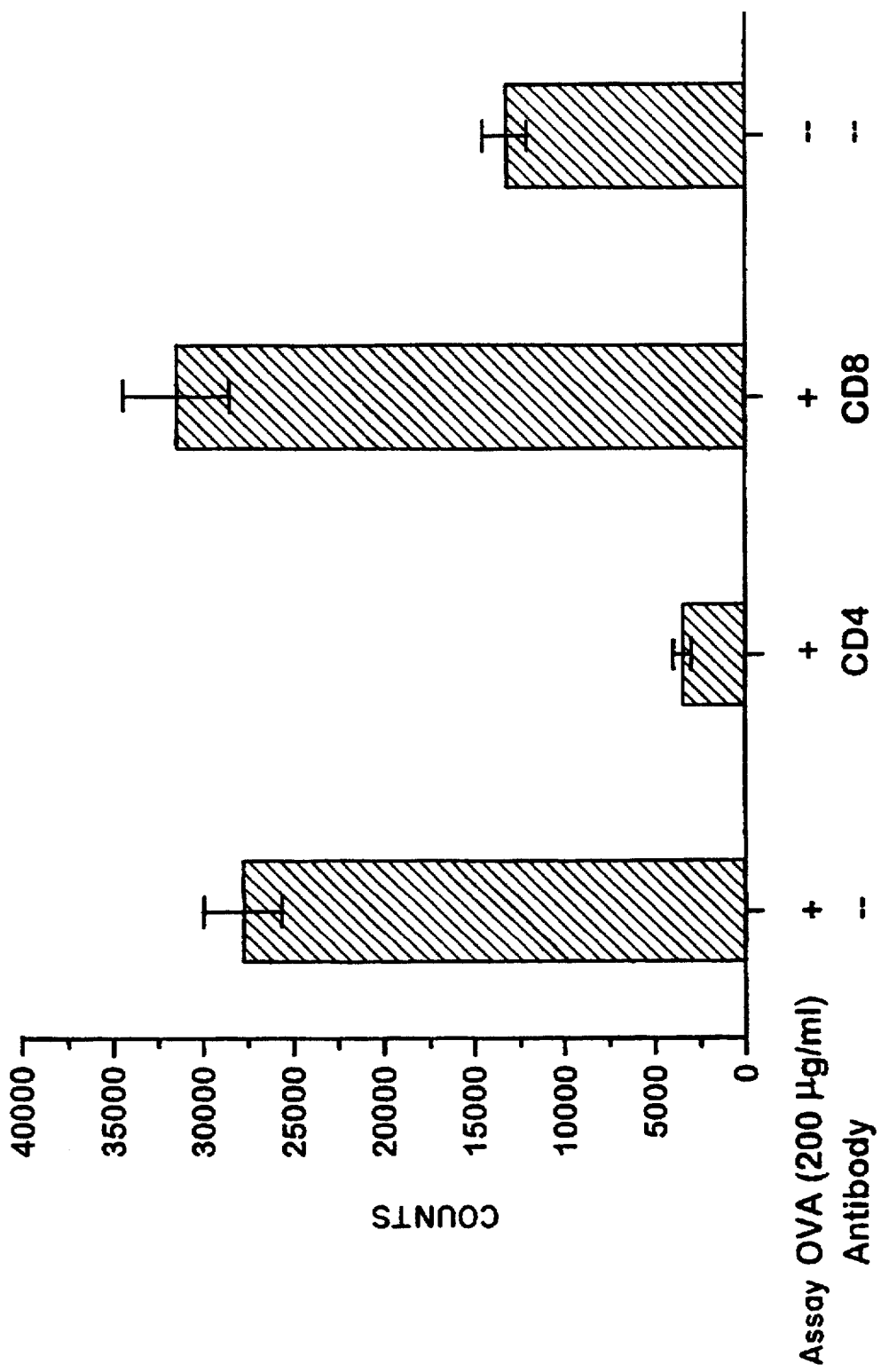
FIG. 3 is a graphic illustration of OVA antigen specific T cell proliferation after exposure to OVA antigen, of mouse spleen cells from mice dosed by oral gavage with OVA antigen, and modified amino acid carrier. (Group 3 (1 priming dose)).
Figure 4:
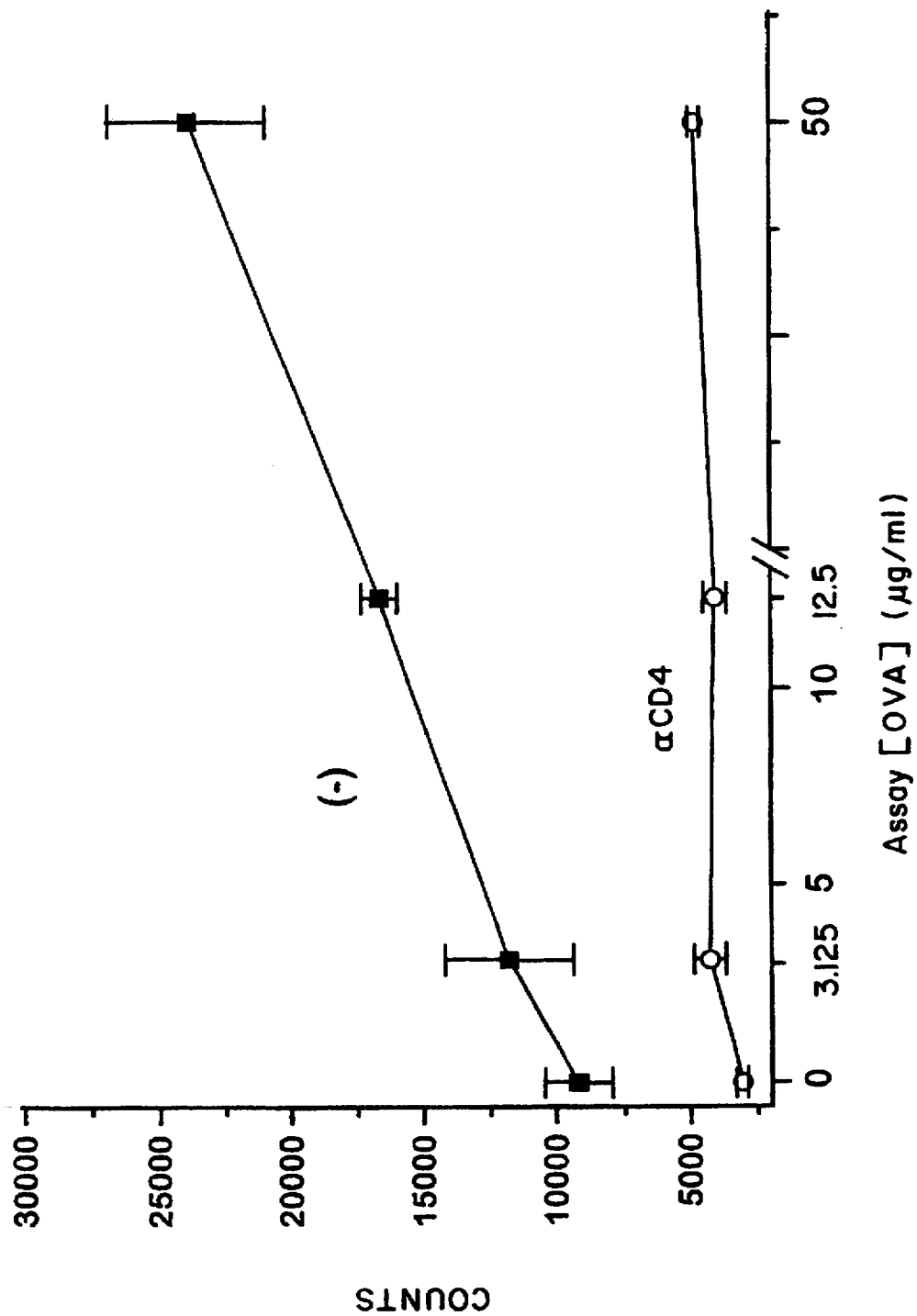
FIG. 4 is a graphic illustration of OVA antigen specific T cell proliferation after exposure to varying concentrations of OVA antigen, of mouse spleen cells from mice dosed by oral gavage with OVA antigen and modified amino acid carrier. (Control (unimmunized)).

The results of assays of cells with an assay OVA antigen concentration of 200 μg/ml from mouse groups 1, 2, and 3 are illustrated in FIGS. 1, 2, and 3, respectively. Results from assays of cells from mouse group 3 with varying concentrations of assay OVA antigen are illustrated in FIG. 4.

COMPARATIVE EXAMPLE 15A

Figure 5:
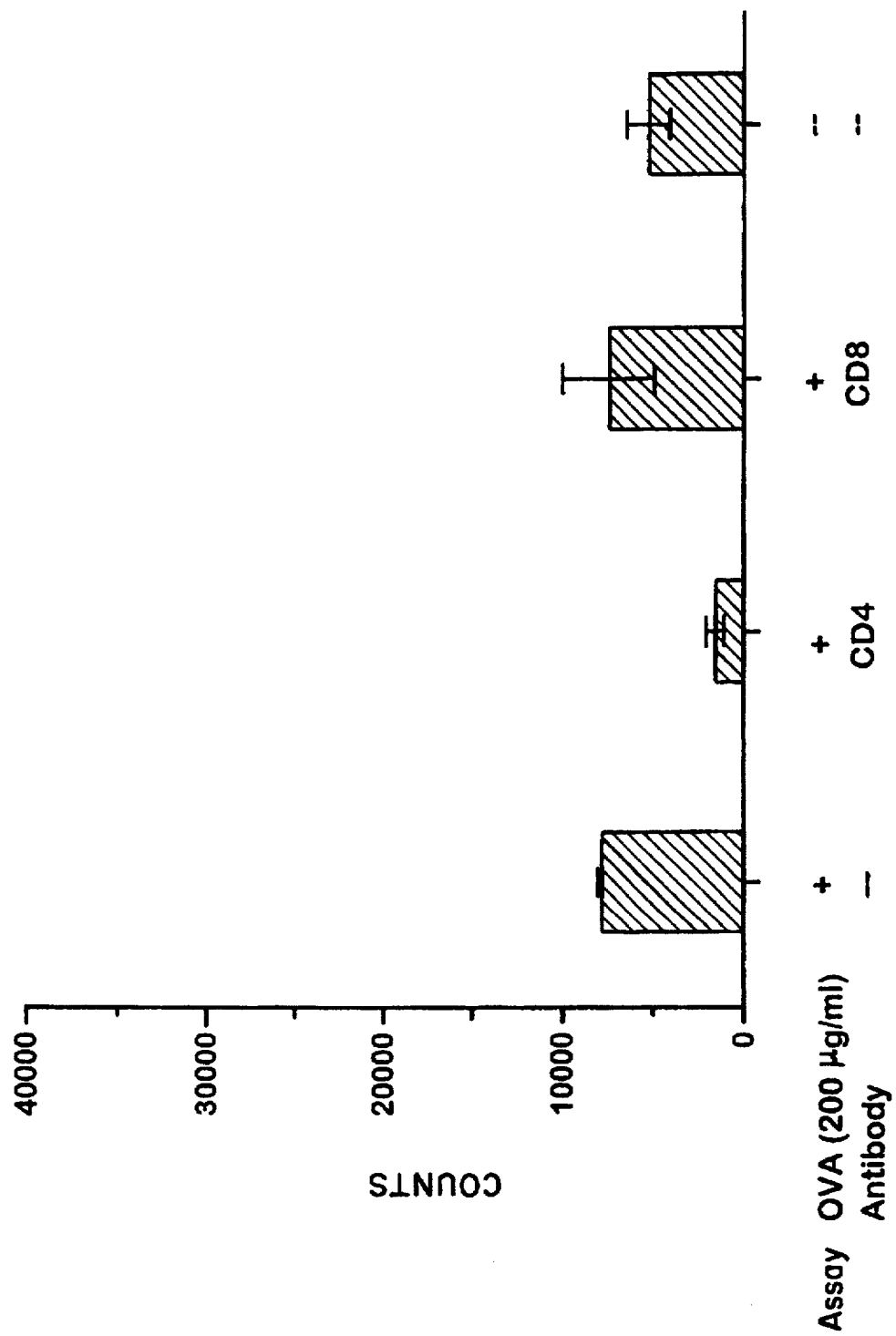
FIG. 5 is a graphic illustration of OVA antigen specific T cell proliferation after exposure to OVA antigen, of mouse spleen cells from a control group of mice.
Figure 6:
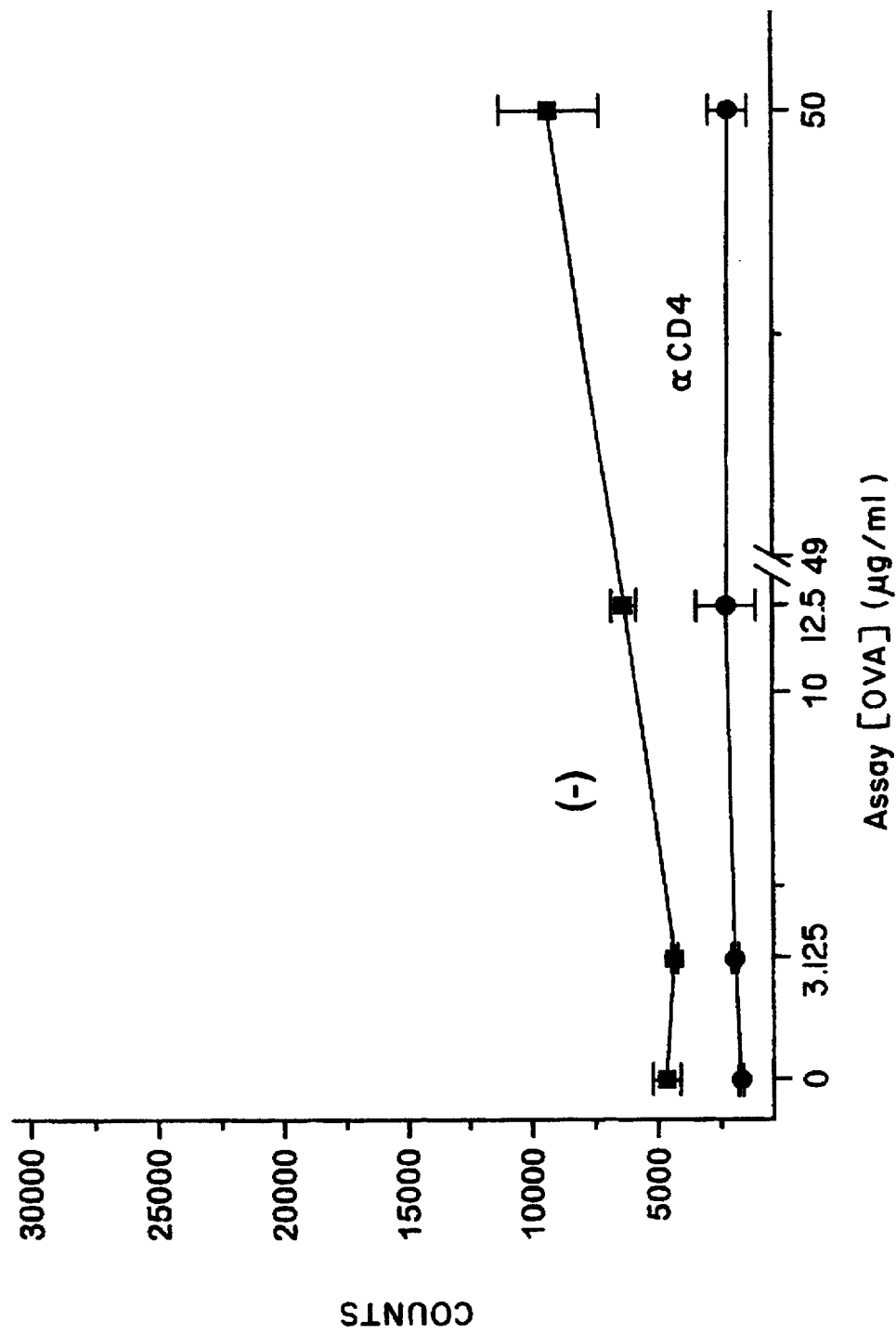
FIG. 6 is a graphic illustration of OVA specific T cell proliferation after exposure to varying concentrations of OVA antigen, of mouse spleen cells from a control group of mice. (Control (unimmunized)).

Non-immunized mice were sacrificed. Spleen cells were obtained and assayed according to the procedure of Example 15. The results of assays with an assay OVA antigen concentration of 200 μg/ml are illustrated in FIG. 5. The results of assays with varying concentrations of assay OVA antigen are illustrated in FIG. 6.

EXAMPLE 16

ANTIGEN IN VIVO EXPERIMENT IN MICE

Mice were administered an antigen/carrier composition prepared according to the method of Example 14. Blood samples were taken from the mice of Groups 1, 2, and 3 of Example 15 on day 52 after the initial priming dose. Serum was assayed using an ELISA according to the procedure below to measure anti-OVA serum IgG induction.

SERUM IgG TITER DETERMINATION

(USE ONLY INNER WELLS ON SINGLE UNIT PLATES)

1. Add 100 μl OVA solution (4 μg/ml in carbonate buffer, pH 9.6) to each well.
2. Incubate at 4° C. overnight, or 2 hours at room temperature with shaking.
3. Empty and wash plate 4 times with imidazole buffer having 0.05% Tween 20, with one 5 minute soak.
4. Add 300 μl of BSA solution and incubate 30 minutes at room temperature.
5. Wash as above.
6. Add 100 ml of 1/15 diluted BSA solution to each well except first row of samples, first standard curve well, and wells for positive and negative controls.
7. Add samples and controls.

Samples: Place 150 μl of a 1/200 dilution of each sample in first well of sample rows.

Serially dilute 50 μl for 3-fold dilutions.

Positive Controls: Place 200 µl of hyper immune serum at 1/2000 dilution in first well. Serially dilute 100 µl two-fold to 1/64000 (6 wells).

Negative control: pooled serum from naive mice (1/200 dilution): 100 µl.

"Background": all reagents except serum in at least two wells.

8. Incubate two hours at room temperature with shaking.

9. Wash 8 times with imidazole buffer having 0.05% Tween 20, with one 5 minute soak.

10. Add 100 µl of Goat anti-Mouse IgG Alkaline Phosphatase Conjugate (diluted 1/1000 in 1/15 PBS/BSA solution containing 4% PEG 6000)

11. Incubate overnight at 4° C. after shaking for a few minutes.

12. Wash 8 times with imidazole buffer having 0.05% Tween 20.

13. Add 100 µl of freshly prepared pNPP solution to each well and develop at room temperature in the dark.

14. Read $OD_{405}$.

15. Record when $OD_{405}$ of 1/2000 standard=1.2 (about 0.5–1 hour).

Figure 7:
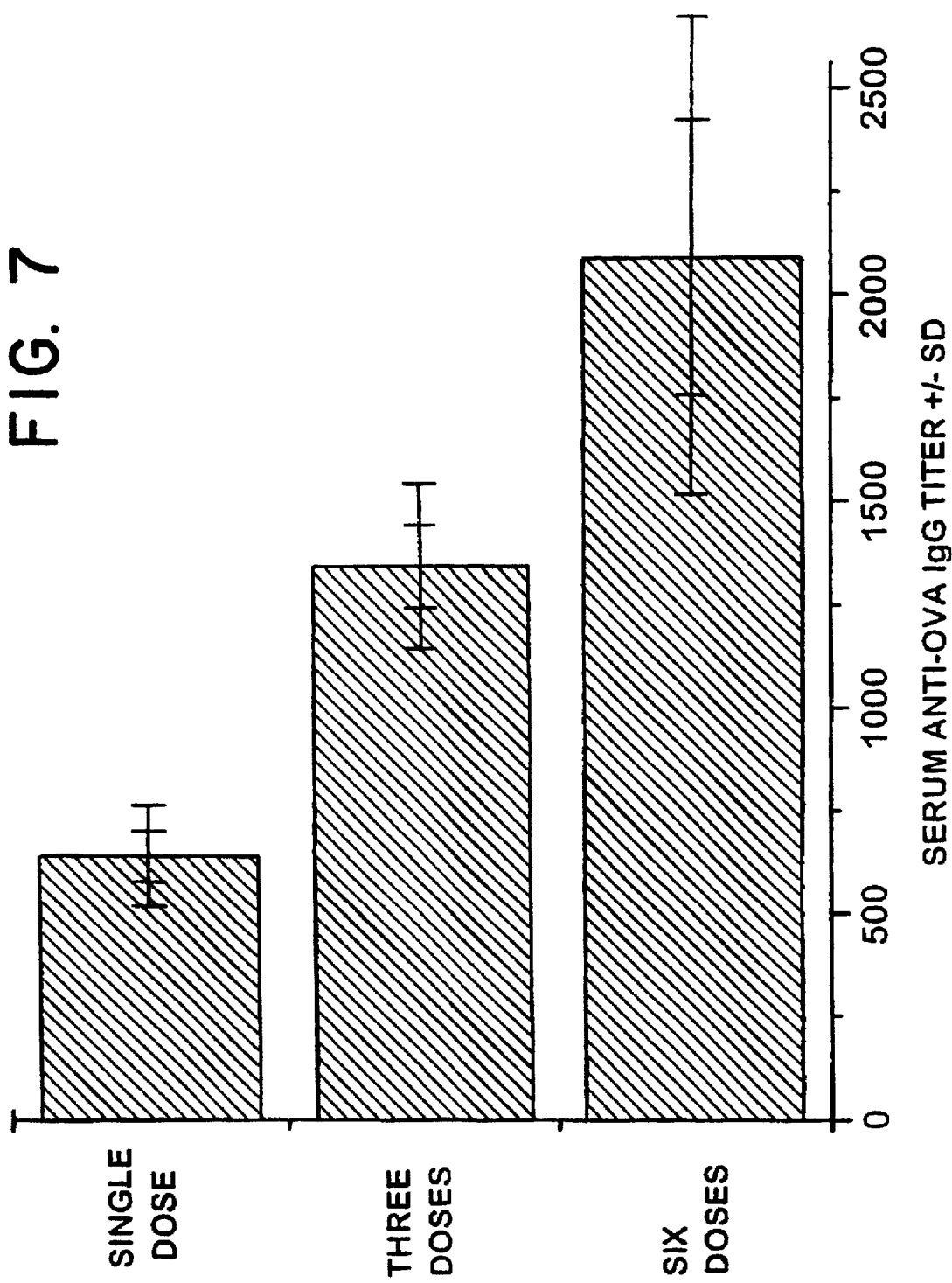
FIG. 7 is a graphic illustration of anti-OVA IgG titers induced in mice dosed by oral gavage with OVA antigen and a mixture of N-cyclohexanoyl-(I)-tyrosine and N-cyclohexanoylleucine. (Serum Anti-OVA IgG titers—42 days after final dose (day 52); 0.1 mg OVA/dose).

16. Calculate antibody titers in samples by interpolation of OD's of dilutions. (max dilution at which $OD_{405}$ =3× background). Results are illustrated in FIG. 7.

EXAMPLE 17

ANTIGEN IN VIVO EXPERIMENTS IN MICE

Mice were administered a subcutaneous prime with OVA antigen (10 µg) and ten days later, were administered an oral booster (100 µg OVA antigen and 10 mg of a sulfonated amino acid mixture prepared according to the method of Example 10).

Serum from blood drawn at 2, 2.5, 5, 6, 10, 12, 14, and 16 weeks following the priming dose, was assayed by ELISA according to the procedure of Example 16 to measure anti-OVA serum IgG titers.

Results are illustrated in FIG. 8.

All patents, applications, publications, and test methods cited herein are hereby incorporated by reference.

Many variations of the present invention will suggest themselves to those skilled in the art in light of the above detailed disclosure. All such modifications are within the full intended scope of the appended claims.

What is claimed is:

1. A composition comprising:
   (a) an antigen; and
   (b) at least one carrier comprising a member selected from the group consisting of:
      (i) an acylated amino acid;
      (ii) a poly amino acid comprising at least one acylated amino acid;
      (iii) a sulfonated amino acid;
      (iv) a poly amino acid comprising at least one sulfonated amino acid; or
      (v) any combination thereof.

2. A composition as defined in claim 1, comprising a mixture.

3. A composition as defined in claim 1, comprising a microsphere.

4. A composition as defined in claim 1, wherein said antigen comprises a peptide.

5. A composition as defined in claim 1, wherein said carrier comprises an acylated amino acid.

6. A composition as defined in claim 1, wherein said carrier comprises a poly amino acid comprising at least one acylated amino acid.

7. A composition as defined in claim 1, wherein said carrier comprises a sulfonated amino acid.

8. A composition as defined in claim 1, wherein said carrier comprises a poly amino acid comprising at least one sulfonated amino acid.

9. A composition comprising:
   (a) ovalbumin; and
   (b) at least one carrier comprising a member selected from the group consisting of:
      (i) an acylated amino acid;
      (ii) a poly amino acid comprising at least one acylated amino acid;
      (iii) a sulfonated amino acid;
      (iv) a poly amino acid comprising at least one sulfonated amino acid; or
      (v) any combination thereof.

10. A dosage unit form comprising
    (A) a composition as defined in claim 1; and
    (B) (a) an excipient,
        (b) a diluent,
        (c) a disintegrant,
        (d) a lubricant,
        (e) a plasticizer,
        (f) a colorant,
        (g) a dosing vehicle, or
        (h) any combination thereof.

11. A dosage unit form as defined in claim 10 comprising a tablet, a capsule, or a liquid.

12. A method for administering an antigen to an animal, said method comprising orally administering to said mammal a composition as defined in claim 1.

13. A method for preparing a composition as defined in claim 1, said method comprising mixing an antigen, and a carrier comprising a member selected from the group consisting of:
    (i) an acylated amino acid;
    (ii) a poly amino acid comprising at least one acylated amino acid;
    (iii) a sulfonated amino acid;
    (iv) a poly amino acid comprising at least one sulfonated amino acid; or
    (v) any combination thereof.

* * * * *